(12) United States Patent
Seguro et al.

(10) Patent No.: US 9,292,636 B2
(45) Date of Patent: *Mar. 22, 2016

(54) METHOD FOR MODELING AN EXUDATE ON A SUBSTRATE

(71) Applicant: The Procter & Gamble Company, Cincinnati, OH (US)

(72) Inventors: Jean Vittorio Seguro, Cincinnati, OH (US); Joseph F. Kitching, Middletown, OH (US)

(73) Assignee: The Procter & Gamble Plaza, Cincinnati, OH (US)

( * ) Notice: Subject to any disclaimer, the term of this patent is extended or adjusted under 35 U.S.C. 154(b) by 462 days.

This patent is subject to a terminal disclaimer.

(21) Appl. No.: 13/718,162

(22) Filed: Dec. 18, 2012

(65) Prior Publication Data

US 2014/0172381 A1    Jun. 19, 2014

(51) Int. Cl.
*G06G 7/48* (2006.01)
*G06F 17/50* (2006.01)
*A61F 13/15* (2006.01)

(52) U.S. Cl.
CPC ............ *G06F 17/5018* (2013.01); *A61F 13/15* (2013.01); *G06F 2217/16* (2013.01)

(58) Field of Classification Search
CPC .................................................. G06F 17/5018
USPC ............................................................ 703/7
See application file for complete search history.

(56) References Cited

U.S. PATENT DOCUMENTS

| | | | |
|---|---|---|---|
| 7,099,734 B2 | 8/2006 | Pieper et al. | |
| 7,569,041 B2 | 8/2009 | Stupperich et al. | |
| 7,684,939 B2 | 3/2010 | Allende-Blanco et al. | |
| 7,979,256 B2 | 7/2011 | Macura et al. | |
| 8,386,219 B2 * | 2/2013 | Koehler et al. | 703/6 |
| 2004/0236455 A1 | 11/2004 | Woltman et al. | |
| 2004/0236457 A1 | 11/2004 | Stabelfeldt et al. | |
| 2004/0236552 A1 | 11/2004 | Pieper et al. | |
| 2005/0256686 A1 | 11/2005 | Stabelfeldt et al. | |
| 2008/0046189 A1 | 2/2008 | Allende-Blanco et al. | |
| 2011/0060555 A1 * | 3/2011 | Koehler et al. | 703/1 |

FOREIGN PATENT DOCUMENTS

EP        1621167 A2     2/2006

OTHER PUBLICATIONS

"Parallel finite element methods for modeling contact in geometrically nonlinear membrane structures; Xu, Zhenlong (Ph.D); Accorsi, Michael L. (adviser); DisserationAbstracts International (2002), vol. 63, No. 8B, p. 3835. (2 pages)".
"Mechanics of Thin, Flexible, Translating Media and Their Interactions with Surrounding Air; Muftu, S.; JSME International Journal, Series C (MechanicalSystems, Machine Elements and Manufacturing) Sep. 2005, vol. 48, No. 3, p. 329-336".
"Computer Modeling of Woven Fabrics; Toney, M.; Skelton J.; The Fiber Society, A Joint International Conference with: The Textile Institute, Institute of Materials (UK,F), Ensitm-Mulhouse (F), Institut Textile de France (F), Spring 1997 JointConference,: 177+,3 pages (Apr. 21-24, 1997)".

* cited by examiner

*Primary Examiner* — Hugh Jones
(74) *Attorney, Agent, or Firm* — Andres E. Velarde

(57) ABSTRACT

Methods of using computer based models for simulating the physical behavior of bodily exudates with absorbent articles.

9 Claims, 14 Drawing Sheets

METHOD FOR MODELING AN EXUDATE ON A SUBSTRATE

FIELD OF THE INVENTION

In general, the present disclosure relates to computer based models for substrates. In particular, the present disclosure relates to methods of using computer based FSI models for simulating the physical behavior of bodily exudates with a substrate. The exudates may be Non-Newtonian or Newtonian.

BACKGROUND OF THE INVENTION

Designers of absorbent articles have traditionally relied upon results from physical testing of prototypes to evaluate the performance of absorbent articles and as a basis for making design changes. Developing prototypes of absorbent articles can be expensive because the equipment necessary to manufacture the absorbent article may not be developed at the time when new absorbent articles are being designed. In some instances, the materials from which the absorbent article will be constructed have yet to be developed. Furthermore, physical testing often requires working in a controlled laboratory environment, which can be expensive. In the case of hygienic products, such as catamenial devices, wound dressings, facial tissue, diapers, and diaper wipes, laboratory personnel may be exposed to increased risks to their health as a result of handling animal exudates during laboratory tests. For absorbent articles designed to absorb other materials, physical testing may require that laboratory personnel be exposed to unhealthy chemicals that the absorbent article is designed to absorb.

Obtaining data describing the transient behavior of absorbent articles can be challenging. Often, a designer of absorbent articles is interested in how the absorbent article being designed acquires exudate at the onset of exposure to an exudate. By the time the designer removes the absorbent article from exposure to the exudate, dissects the absorbent article, places portions of the absorbent article in a device capable of measuring distribution of exudate, and measures the distribution of the exudate, the distribution of the exudate can change significantly as compared to the distribution of exudate when the absorbent article was removed from contact with the exudate.

In some design processes for designing absorbent articles based on physical testing, physical testing on replicates of absorbent articles is needed to deduce conclusions based on observed results from testing. Testing replicates can help reduce uncertainty in making evaluations of different designs for absorbent articles and making decisions on how to improve the design of an article. Creating prototypes that are precise replicates of one another can be challenging. When prototypes are not precise replicates of one another, interpreting testing results can be more difficult.

The fluid transport properties of absorbent materials commonly used in absorbent articles can be difficult to measure. Key fluid transport properties, which partially describe interactions between the absorbent and exudate, include the capillary pressure versus saturation function and the relative permeability function. Most commonly used methods for measuring the absorbent-fluid interaction properties are not suitable for testing with fluids other than water. Further, most methods run an iterative computation wherein the exudate is placed in contact, the substrate is allowed to react, and then the exudate reacts to the substrate. This iteration repeats itself until the model has ended. While this iteration is a good approximation, it does not fully model the real world interaction wherein the exudate and the substrate react simultaneously to each other. Also, unlike the previously modeled exudates, many bodily exudates may take the form of a Non-Newtonian fluid and/or a mixture of fluids and solid components.

There is a continuing unaddressed need for methods for developing absorbent articles that integrates physical measurements of the absorbent properties of absorbent materials into the design process.

Additionally, there is a continuing unaddressed need for virtual product development methods that allow the product developer to gather data on the distribution of Non-Newtonian exudates when placed in contact with the absorbent article while simultaneously changing the properties of the substrate in contact with the Non-Newtonian fluid and/or a mixture of fluids and solid components.

Further, there is a continuing unaddressed need for methods for developing absorbent articles that do not rely entirely on physical testing of prototypes.

There is also a continuing unaddressed need for product designers to be able to test absorbent materials and designs for absorbent articles without having to expose personnel to the substances absorbent articles are designed to absorb.

SUMMARY OF THE INVENTION

A method of simulation that includes representing at least a portion of a substrate with a computer based model. The substrate is represented by a plurality of elements with each of the elements including an amount of the substrate. The method further includes representing a domain space including the substrate. The method includes transforming the substrate to fit the domain space. The method includes representing a bodily exudate into the domain space with a computer based model of the bodily exudate. The method also includes transforming the model of the substrate to form a computer based model on the distribution of the bodily exudate using finite element analysis. The transformation of the substrate is simultaneous to the distribution of the bodily exudate.

DETAILED DESCRIPTION OF THE INVENTION

Figure 1:
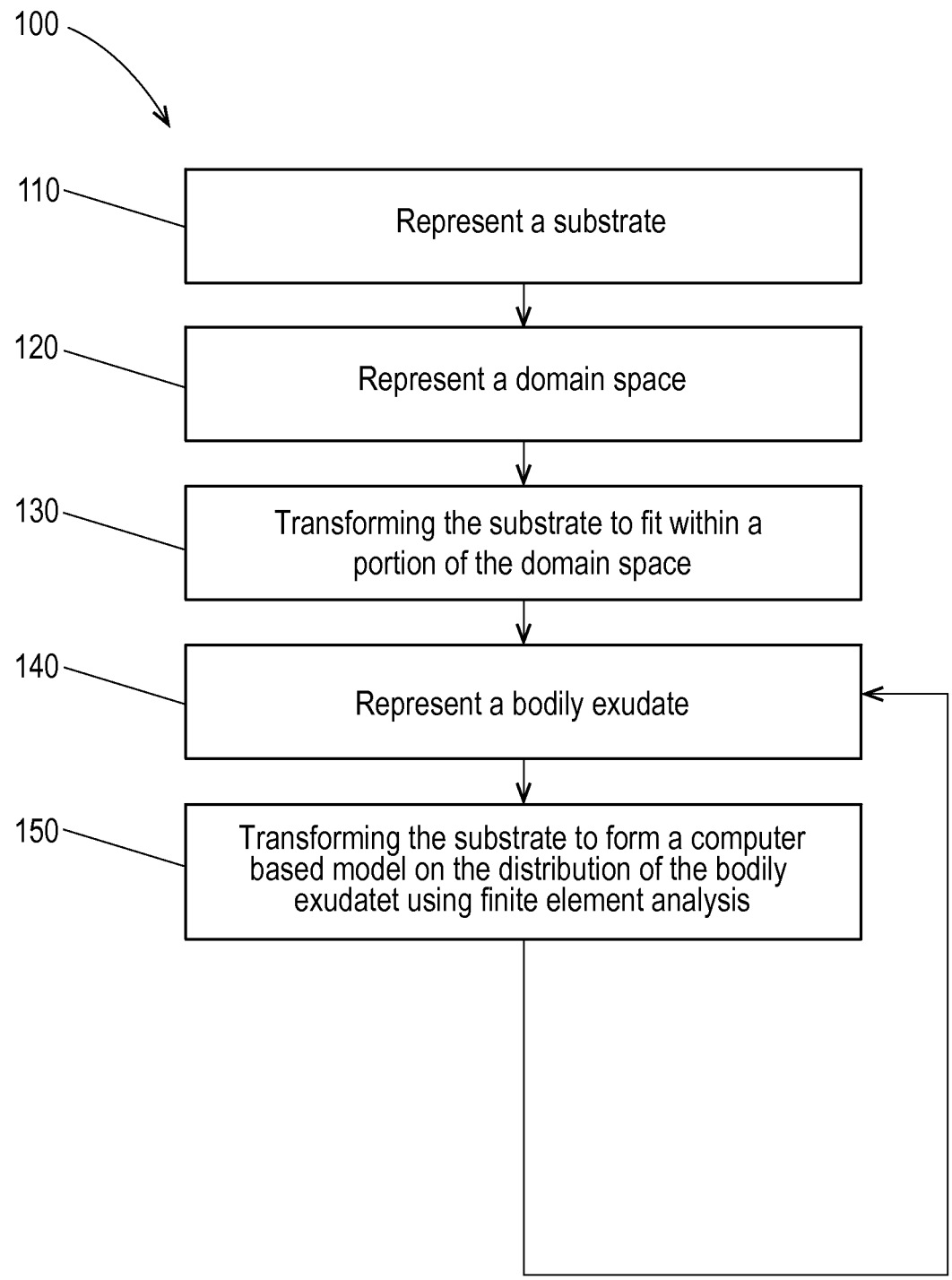
FIG. 1 is a chart illustrating a method of using computer based models for simulating the physical behavior of bodily exudate with an absorbent article.

As used herein "exudate" refers to a natural or synthetic substance that may be absorbed and/or contained into or onto an absorbent article. Non-limiting specific examples of a exudate include fluids such as, for example, artificial menstrual fluid, menstrual fluid, vaginal discharge, synthetic vaginal discharge, urine, synthetic urine, bowel movement fluids, sweat, and synthetic sweat. Exudates also include solids such as, for example, feces, solid bowel movements, and protinaceous menses.

As used herein, the term "free bodily fluid" refers to a bodily fluid that is not absorbed within an absorbent material, but is free to move in, on, or through the absorbent article or be absorbed by the absorbent material.

As used herein, a "Non-Newtonian fluid" is a fluid whose flow behavior departs from that of a Newtonian fluid, so that the rate of shear is not proportional to the corresponding stress.

As used herein, a "Newtonian fluid" is a fluid whose stress versus strain rate curve is linear and passes through the origin. An example of a Newtonian fluid is water.

As used herein "saturation" refers to the fraction of the void space in an absorbent filled by the fluid. Saturation can be reported as a percentage or in decimal form.

The present disclosure includes methods of simulating the physical behavior of an exudate with an absorbent article containing both porous media and a non-porous media. The exudates may be a fluid, a solid, or a mixture of solid and fluid components. The fluid may be Newtonian. The fluid may be Non-Newtonian. The present disclosure can at least assist in predicting whether or not a particular absorbent article design can adequately contain and distribute bodily exudates. As a result, particular absorbent article designs and absorbent materials can be evaluated and modified as computer based models before they are tested as real world things.

Fluid structure interaction (FSI) may be used to model the virtual system. FSI can be broken down into computer aided engineering (CAE) and the categories within CAE including, for example, finite element analysis (FEA) and computational fluid dynamics (CFD).

Computer aided engineering (CAE) is a broad area of applied science in which technologists use software to develop computer based models that represent real world things. The models can be transformed to provide information about the physical behavior of those real world things, under certain conditions and/or over particular periods of time. With CAE, the interactions of the computer based models are referred to as simulations. Sometimes the real world things are referred to as a problem and the computer based model is referred to as a solution. There are several major categories of CAE.

Finite element analysis (FEA) is a major category of CAE. In FEA, models representing mechanical articles, as well as their features, components, structures, and/or materials are transformed to predict stress, strain, displacement, deformation, and other mechanical behaviors. FEA represents a continuous solid material as a set of discrete elements. In FEA, the mechanical behavior of each element is calculated, using equations that describe mechanical behavior. The results of all of the elements are summed up, to represent the mechanical behavior of the material as a whole.

Commercially available software can be used to conduct FEA. LSDYNA and ABAQOS are two examples of FEA software. Alternatively, FEA software can be written as custom software or may be open source code software. FEA software can be run on various computer hardware, such as a personal computer, a minicomputer, a cluster of computers, a mainframe, a supercomputer, or any other kind of machine on which program instructions can execute to perform FEA functions.

Computational fluid dynamics (CFD) is another major CAE category. In CFD, models representing fluids (e.g. liquids and/or gases) are transformed to predict pressure, flow rate, velocity, temperature, and other fluid and/or thermal properties. CFD also represents a continuous fluid material as a set of discrete elements. A CFD element is often referred to as a cell, a finite difference cell, or a finite volume. However, for ease of reference, the term element is used throughout the present disclosure for CFD models. Unless otherwise stated, a reference to an element, in context of CFD, can refer to a cell, a finite difference cell, or a finite volume, as will be understood by one of ordinary skill in the art. In CFD, the fluid behavior is calculated for the elements, using equations that describe fluid behavior. For example, CFD often employs the Navier-Stokes equations, or variations thereof. The equations are solved iteratively, to represent the fluid behavior of the material as a whole.

Commercially available software can be used to conduct CAE. Fluent, from ANSYS, Inc. in Canonsburg, Pa., Flow3D, from Flow Science, Inc. in Santa Fe, N. Mex., and FeFlow from DHI-WASY in Berlin, Germany are examples of commercially available CFD software. Alternatively, CAE software can be written as custom software or may be open source code software, for example, OpenFOAM. CAE software can be run on various computer hardware, such as a personal computer, a minicomputer, a cluster of computers, a mainframe, a supercomputer, or any other kind of machine on which program instructions can execute to perform CAE functions.

CAE software can represent a number of real world things, such as substrates. Substrates may be used as part of an absorbent article. The substrate can be a woven material, a nonwoven material, a cellulosic material, a polymer film or an apertured polymer film. An absorbent article can receive, contain, and absorb bodily exudates (e.g. urine, menses, feces, etc.). Absorbent articles include products for sanitary protection, for hygienic use, and the like. Fluids modeled may be Newtonian or Non-Newtonian.

Representative absorbent articles may be wearable, non-wearable, reusable, and/or disposable. Representative absorbents can be an absorbent article. An absorbent article can be a catamenial device comprising a topsheet, a backsheet, and an absorbent core disposed between the topsheet and backsheet. The absorbent article can be a diaper. The absorbent article can dispense a substance. The absorbent article can be selected from the group consisting of pull-on diapers, training pants, incontinence products, feminine wipes, diaper wipes, floor wipes, countertop wipes, body wipes, toddler wash wipes, bath tissues, breast pads, paper towels, toilet paper, facial tissue, wound dressings, handkerchiefs, household wipes, foam, and chamois. Some absorbent articles are wearable. A wearable absorbent article is configured to be worn on or around a lower torso of a body of a wearer. Examples of wearable absorbent articles include diapers and incontinence undergarments.

Some absorbent articles are disposable. A disposable absorbent article is configured to be disposed of after a single use (e.g., not intended to be reused, restored, or laundered). Examples of disposable absorbent articles include disposable diapers, disposable incontinence undergarments, as well as feminine care pads and liners.

Some absorbent articles are reusable. A reusable absorbent article is configured to be partly or wholly used more than once. A reusable absorbent article is configured such that part or all of the absorbent article is durable, or wear-resistant to laundering, or fully launderable. An example of a reusable absorbent article is a diaper with a washable outer cover.

The absorbent article can have an absorbent. The absorbent can be selected from the group consisting of nonwovens, wovens, apertured polymer films, cellulosic materials, thermoplastic materials, air laid materials, sponges, absorbent gelling materials, foams, rayon, cotton, airfelt, creped cellulose wadding, meltblown polymers, and peat moss.

CAE can be used to design, simulate, and/or evaluate all kinds of absorbent articles, their features, materials, structures, and compositions, as well as their performance characteristics, such as swelling and deformation.

FIG. 1 is a chart illustrating a method 100 of steps 110-150 for using computer based models for simulating the physical behavior of exudates placed onto an absorbent material. Although the steps 110-150 are described in numerical order in the present disclosure, some or all of these steps can be performed in other orders, and/or at overlapping times, and/or at the same time, as will be understood by one of ordinary skill in the art. The method can also include transforming the fitted, absorbent article by simulating the swelling of the fitted absorbent article from a bodily fluid.

The method 100 includes a first step 110 of representing at least a portion of a substrate with a computer based model. The computer based model can represent an absorbent article. The model can represent a fastenable absorbent article, or a pant-type absorbent article, or a feminine pad, or another kind of absorbent article. The model of the absorbent article can be created as described in connection with FIGS. 2A-2C. In the first step 100, the model may represent the absorbent in a dry state, wherein the absorbent article has not been wetted or soiled. Alternatively, in the first step 100, the model may represent the absorbent article in a wet state, wherein the substrate has been partially wetted or soiled.

The method includes a second step 120 of determining a domain space with a computer based model. The domain space is defined by boundary conditions including the substrate. The domain space can be the virtual space to be filled by the exudate. The domain space can represent a human body with a computer based model. The model can represent an entire human body or can represent one or more portions of a human body. If the model represents only a portion of a human body, then the model should represent one or more portions of a human body to which the absorbent article of the first step 110 is intended to be fitted. The model can represent a male human body, or a female human body, or an androgynous human body (lacking gender specific anatomical features). The model of the human body can be created as described in connection with FIGS. 3A-3B.

The method 100 includes a third step 130 of transforming the absorbent article by simulating a fitting of the absorbent article to a portion of the domain space using FEA. The transforming of the third step 130 includes a mechanical interaction between the model of the absorbent article from the first step 110 and the model of the domain space of the second step 120. Prior to or during the third step 130, these models can be brought together. For a wearable absorbent article fitted to a human model, the fitting is a donning of the absorbent article. For a feminine pad or liner, the fitting is a placement of the absorbent article in an in-use position. The fitting simulated in the third step 130 can be performed as described in connection with FIGS. 4A-4C.

In the fitting simulated in the third step 130, FEA program instructions can execute to simulate the mechanical interaction between the model of the absorbent article from the first step 110 and a model of the human body of the second step 120. However, the present disclosure contemplates that, part, or parts, or all of the third step 130 can be performed using another kind of computer based program instructions, as will be understood by one of skill in the art. The simulation of the third step 130 transforms the model of the absorbent article from the first step 110 and the model of the human body of the second step 120 to form a computer based model that represents a fitted absorbent article. For a wearable absorbent article, the simulation of the third step 130 results in a model that represents the fitted absorbent article being worn around a lower torso of the human body. For a feminine pad or liner, the simulation of the third step 130 results in a model that represents the fitted absorbent article positioned proximate to a pudendal region of the human body. The simulation of the third step 130 may also result in some deformation in the model of the fitted absorbent article and/or in the model of the human body.

Boundary conditions are defined variables that represent physical factors acting within a computer based model. Examples of boundary conditions include forces, pressures, velocities, and other physical factors. Each boundary condition can be assigned a particular magnitude, direction, and location within the model. These values can be determined by observing, measuring, analyzing, and/or estimating real world physical factors. Computer based models can also include one or more boundary conditions that differ from real world physical factors, in order to account for inherent limitations in the models and/or to more accurately represent the overall physical behaviors of real world things, as will be understood by one of ordinary skill in the art. Boundary conditions can act on the model in various ways, to move, constrain, and/or deform one or more parts in the model.

The method 100 includes a fourth step 140 of representing bodily exudates with a computer based model. The model can represent a bodily fluid such as urine, or menses, or another kind of bodily fluid, or runny feces, or a liquid-like bodily exudate. A model can represent a solid bodily exudate such as feces. The Non-Newtonian exudates may be modeled according to the Herschel-Bulkley fluid model equations. The exudates may be modeled based on the strain rate and the viscosity of the exudate calculated by a rheometer. The model can represent the exudate in any desirable location. The model can represent the exudate at a pee point, an anus, and or from a vaginal canal. The model can represent the exudate within the absorbent article. The method can include an additional step of representing a second bodily exudate with a computer based model. The second bodily exudate can be represented simultaneously with the first bodily exudate or after the first bodily exudate.

The method 100 includes a fifth step 150 of transforming the fitted absorbent article by simulating a provision of a bodily exudate to the fitted absorbent article. Simulating a provision of bodily exudate can include determining the location or entrance point of the exudate and the rate at which the exudate is dispensed. The exudate may be dispensed from a virtual pee point, a virtual anus, or a virtual vaginal canal all located on either a male virtual body or a female virtual body. The exudate may be Newtonian or Non-Newtonian.

Prior to or during the fifth step 150, these models can be brought together. The simulation of the fifth step 150 can include one or more of the following: a flow of the model of the bodily exudate of the fourth step 140 from the model of the human body of the third step 130, a flow of the model of the bodily exudate of the fourth step 140 through a model of air, a flow of the model of the bodily exudate of the fourth step 140 on a surface of the model of the human body of the third step 130, a flow of the model of the bodily exudate of the fourth step 140 on an external surface of the model of the fitted absorbent article of the third step 130, and a flow of the model of the bodily exudate of the fourth step 140 through absorbent material of the model of the fitted absorbent article of the third step 130.

In the provision simulated in the fifth step 150, CFD program instructions can execute to simulate each of these exudate flows, as described in connection with FIG. 5. However, the present disclosure contemplates that, part, or parts, or all of the fifth step 150 can be performed using another kind of computer based program instructions. The simulation of the fifth step 150 transforms the model of the bodily exudate of the of the fourth step 140 and the model of the fitted absorbent article from the third step 130 to form a computer based model that represents a fitted, wet and/or soiled absorbent article. The model of the fitted, wet and/or soiled absorbent article includes a distribution of the bodily exudate on and/or in the absorbent article. The distribution of the bodily exudate on and/or in the absorbent article allows for determining what portions of the model of the human body came in contact with one or more bodily exudates and whether any exudate remains in contact with that portion of the model of the human body. The distribution of the bodily exudate and/or in the absorbent article allows for determining what portions of the substrate came in contact with one or more bodily exudates and whether any exudate remains in contact with that portion of the substrate. The absorbent article transformation can be modeled utilizing sold mechanics Stress-Strain relationships. The exudate is modeled based on exudate dynamics principles including the conservation of mass, energy, and momentum.

After the fifth step 150 is completed, the method can be ended or the method can be extended by repeating one or more of the previous steps. In the method 100, after the fifth step 150 is completed, the fourth and fifth 140-150 steps can be repeated, as indicated by the return arrow in FIG. 1. By following this repeat, the method 100 can be used to simulate multiple insults of a bodily exudate to the absorbent article. In the real world, an absorbent article is often worn by a wearer for a wear cycle that includes more than one insult of a bodily exudate. As a result, by simulating multiple insults of bodily exudate, the method 100 can be used to accurately represent the real-world use of an absorbent article.

The model of the human body of the second step 120 can be constrained to assume one or more particular positions or to assume one or more changes in position, as described herein, during the second step 120 and/or before, during, or after any of the subsequent steps. For example, during the fitting of the third step 130, the model of the human body can be constrained to assume a lying position. As another example, during the fitting of the third step 130, the model of the human body can be constrained to assume change in positions (e.g. a natural body movement).

One or more environmental objects and/or environmental conditions can physically interact with part, or parts, or all of the model of the absorbent article of the first step 110, as described herein, during the first step 110 and/or before, during, or after any of the subsequent steps. For example, during the fitting of the third step 130, a model of a changing surface can physically interact with the model of the absorbent article.

One or more environmental objects and/or environmental conditions can physically interact with part, or parts, or all of the model of the human body of the second step 120, as described herein, during the second step 120 and/or before, during, or after any of the subsequent steps. For example, during the fitting of the third step 130, a model of a changing surface can physically interact with the model of the human body.

One or more environmental objects and/or environmental conditions can physically interact with part, or parts, or all of the model of the bodily exudate of the fourth step 140, as described herein, during the fourth step 140 and/or before, during, or after any of the subsequent steps. For example, during and after the fourth step 140, a model of the force of gravity can physically interact with the model of the bodily exudate.

Figure 2A:
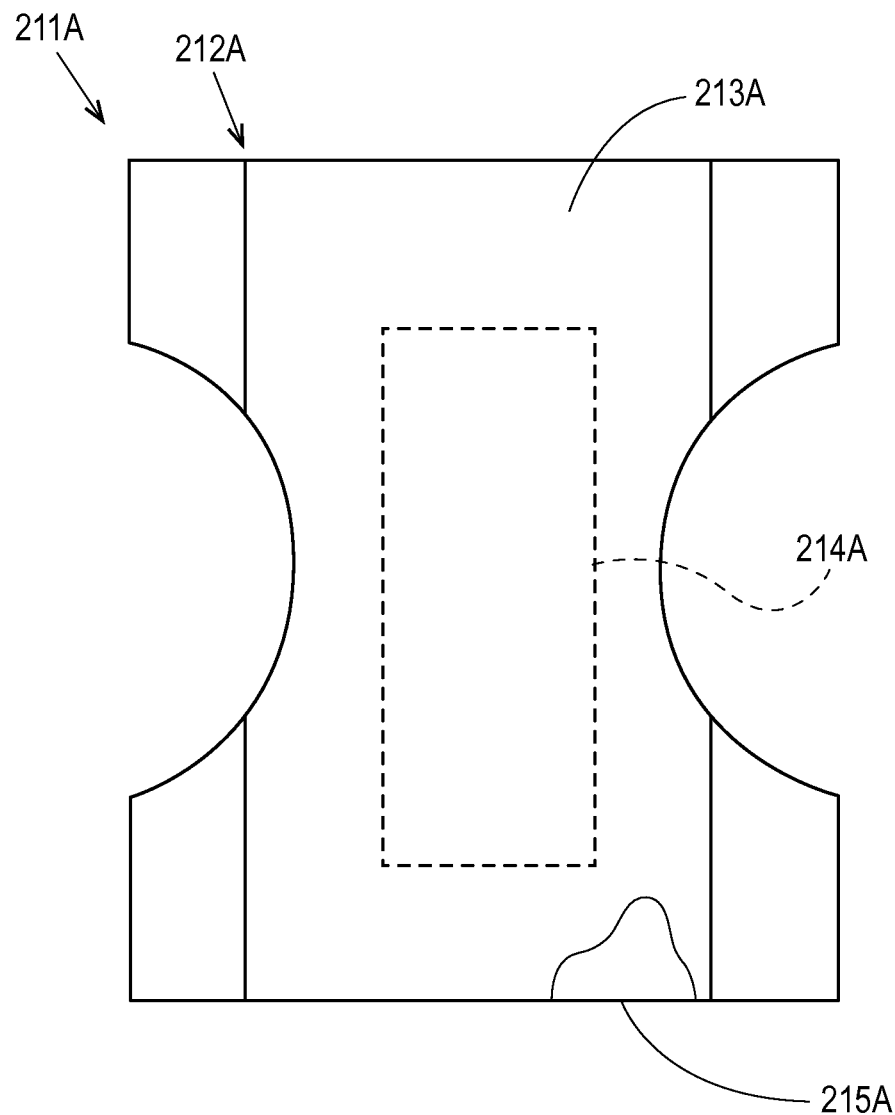
FIG. 2A is an inside plan view illustrating a computer based model representing a pant-type wearable absorbent article.
Figure 2B:
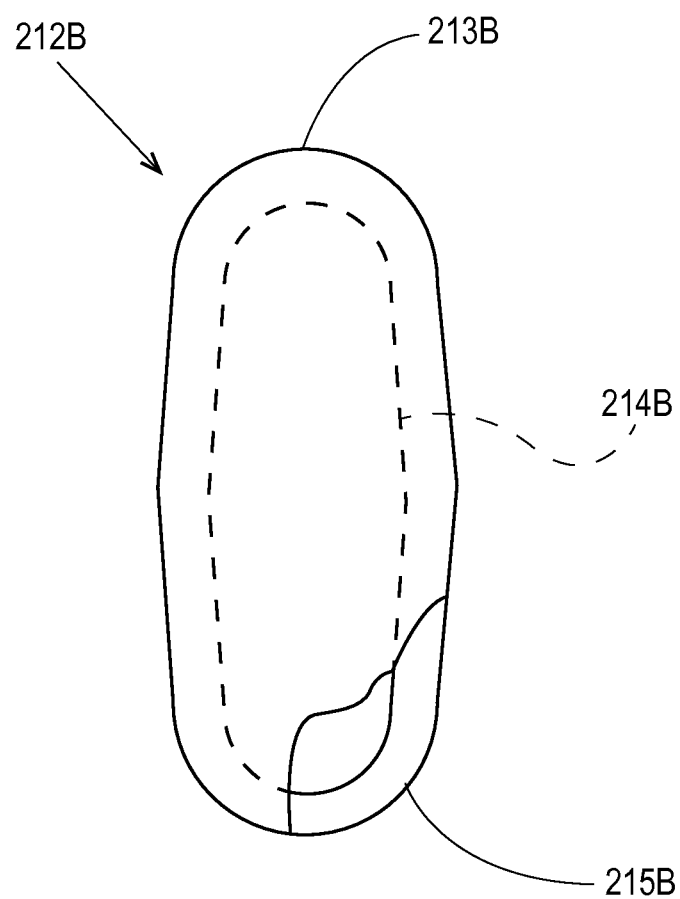
FIG. 2B is an inside plan view illustrating a computer based model representing a feminine pad absorbent article.

FIGS. 2A-2B illustrate computer based models of various absorbent articles. For clarity, FIGS. 2A-2B do not illustrate all details of the absorbent articles.

FIG. 2A is an inside plan view illustrating a computer based model 211A of a pant-type wearable absorbent article 212A. The present disclosure contemplates that, a model of an absorbent article that is configured to be pant-type can be configured to be side-fastenable or without fasteners, as will be understood by one of ordinary skill in the art. Absorbent articles may also be front-fastenable, or rear-fastenable.

The pant-type wearable absorbent article 212A includes a wearer-facing external surface 213A, a garment-facing external surface 215A, and an absorbent material 214A.

The wearer-facing external surface 213A is a layer of one or more materials that form at least a portion of an inside of the pant-type wearable absorbent article and faces a wearer when the absorbent article 212A is worn by the wearer. In FIG. 2A, a portion of the wearer-facing external surface 213A is illustrated as broken-away, in order to show the garment-facing external surface 215A. A wearer-facing external surface is sometimes referred to as a topsheet. The wearer-facing external surface 213A is configured to be liquid permeable, such that bodily exudates received by the absorbent article 212A can pass through the wearer-facing external surface 213A to the absorbent material 214A. A wearer-facing external surface can include a nonwoven material and/or other materials.

The absorbent material 214A is disposed subjacent to the wearer-facing external surface 213A and superjacent to the garment-facing external surface 215A, in at least a portion of the absorbent article 212A. An absorbent material of an absorbent article is part of a structure referred to as an absorbent core. The absorbent material 214A is configured to be liquid absorbent, such that the absorbent material 214A can absorb bodily exudates received by the absorbent article 212A. An absorbent material can include wood pulp, or super absorbent polymers (SAP), or another kind of absorbent material, or any combinations of any of these materials.

The garment-facing external surface 215A is a layer of one or more materials that form at least a portion of an outside of the pant-type wearable absorbent article and faces a wearer's garments when the absorbent article 212A is worn by the wearer. A garment-facing external surface is sometimes referred to as a backsheet. The garment-facing external surface 215A is configured to be liquid impermeable, such that bodily exudates received by the absorbent article 212A cannot pass through the garment-facing external surface 213A. A garment-facing external surface can include a film and/or other materials.

FIG. 2B is an inside plan view illustrating a computer based model 211B of a feminine pad absorbent article 212B. The feminine pad absorbent article 212B includes a wearer-facing external surface 213B, a garment-facing external surface 215B, and an absorbent material 214B, which are each configured in a manner similar to the like-numbered element in FIG. 2A.

Both of the computer based models 211A and 211B can be created as described below, with general references to a computer based model of an absorbent article. A computer based model that represents an absorbent article can be created by providing dimensions and material properties to modeling software and by generating a mesh for the article using meshing software.

A computer based model of an absorbent article can be created with dimensions that are similar to or the same as dimensions that represent parts of a real world absorbent article. These dimensions can be determined by measuring actual samples, by using known values, or by estimating values. Alternatively, a model of an absorbent article can be configured with dimensions that do not represent a real world absorbent article. For example, a model of an absorbent article can represent a new variation of a real world absorbent article or can represent an entirely new absorbent article. In these examples, dimensions for the model can be determined by varying actual or known values, by estimating values, or by generating new values. The model can be created by putting values for the dimensions of parts of the absorbent article into the modeling software.

The computer based model of the absorbent article can be created with material properties that are similar to or the same as material properties that represent a real world absorbent article. These material properties can be determined by measuring actual samples, by using known values, or by estimating values. Alternatively, a model of an absorbent article can be configured with material properties that do not represent a real world absorbent article. For example, a model of an absorbent article can represent a new variation of a real world absorbent article or can represent an entirely new absorbent article. In these examples, material properties for the model can be determined by varying actual or known values, by estimating values, or by generating new values.

The computer based model of the absorbent article can be created with a mesh for the parts of the article. A mesh is a collection of small, connected polygon shapes that define the set of discrete elements in a CAE computer based model. The type of mesh and/or the size of elements can be controlled with user inputs into the meshing software, as will be understood by one of ordinary skill in the art. An external surface of an absorbent article can be created by using shell elements, such as linear triangular elements (also known as S3R elements) with an element size of about 0.1 mm to about 5 mm, about 1 mm to about 4 mm such as, for example, 0.5 mm, 1.5 mm, 2 mm, 2.5 mm, 3 mm, 3.5 mm, 4.5 mm, to represent a nonwoven material. Also, a SAP absorbent material can be created by using solid elements, such as linear hexahedral elements (also known as C3D8R elements) with an element size of about 0.1 mm to about 5 mm, about 1 mm to about 4 mm such as, for example, 0.5 mm, 1.5 mm, 2 mm, 2.5 mm, 3 mm, 3.5 mm, 4.5 mm.

Figure 3A:
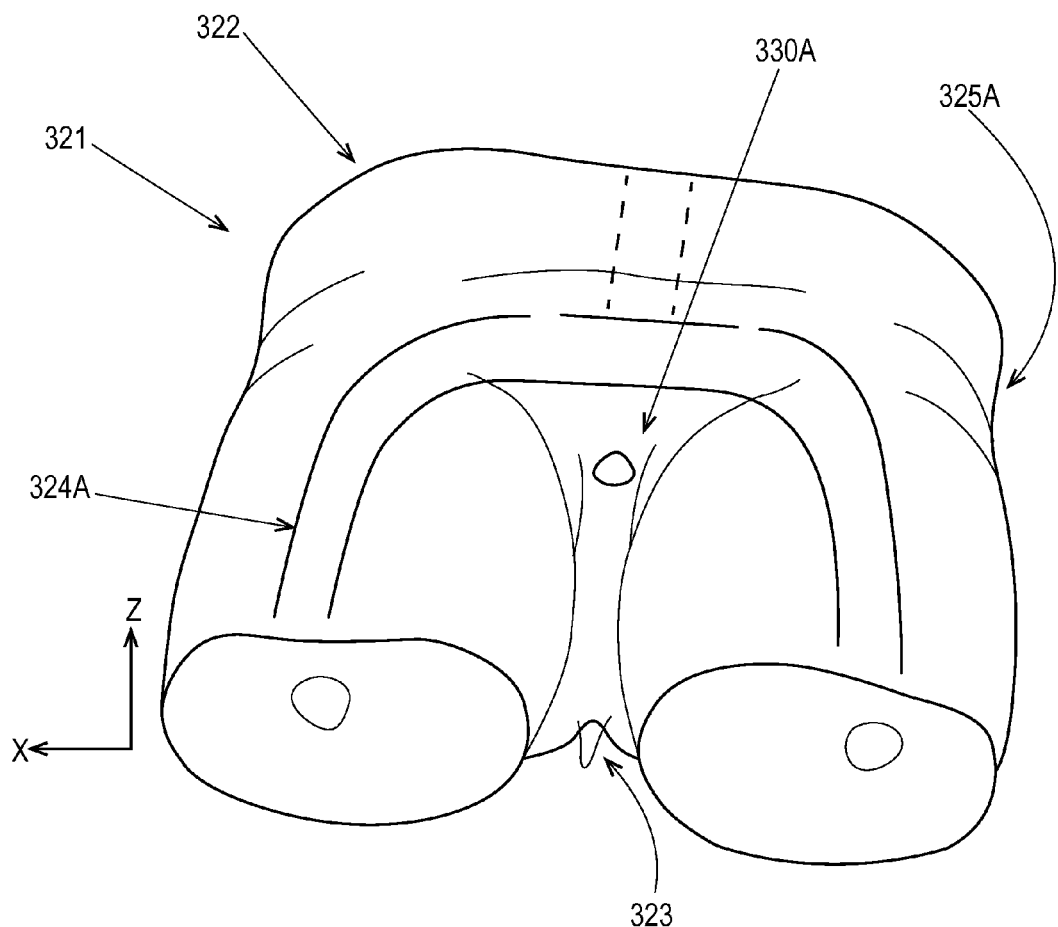
FIG. 3A is a view illustrating a computer based model representing a portion of a male human body.

FIG. 3A is a view illustrating a computer based model 321 that represents a portion of a male human body 322. The male human body 322 includes a male pee point 323, an anus 330A, a support structure 324A, and a flesh structure 325A. The male pee point 323 and the anus 330A are located in anatomically correct locations. The male pee point 323 is located at the urethral opening at the end of the penis. The anus 330A is located in the rear of the model. The support structure 324A provides an approximation of a skeletal system of a human body. The support structure 324A can be configured to allow the male human body 322 to move in a manner that is similar to or the same as real-world movements of the human body.

The flesh structure 325A provides an approximation of the skin, tissue, muscle, and organs of a male human body. The flesh structure 325A is intended to represent the portion of the male human body 322 that is not represented by the support structure 324A. However, the skin, tissue, muscle, and/or organs of a human body can be represented by a number of separate structures.

The flesh structure 324A can be configured to follow the support structure in such movements. The flesh structure 325A can be configured to deform in a manner that is similar to or the same as real-world deformation of the human body.

Wherein the male human body 322 can move, the computer based model of the male human body 321 can be constrained to assume one or more particular positions, or to assume one or more changes in position. The particular positions can include lying down, sitting, on hands and knees, kneeling, standing, or any other position that can represent a real world body position, or variations of any of these. The changing of positions can include twisting, turning, leaning, rocking, rolling, crawling, cruising, walking, jumping, running, or any other change of positions that can represent a real world body movement, or variations of any of these. The changing of positions can be accomplished by moving the model through the positions in series, by moving the model in a discontinuous fashion, or by moving the model in a continuous fashion. The computer based model of the male human body 321 can be configured to assume changes in position that are similar to or the same as a human body's natural range of motion.

Figure 3B:
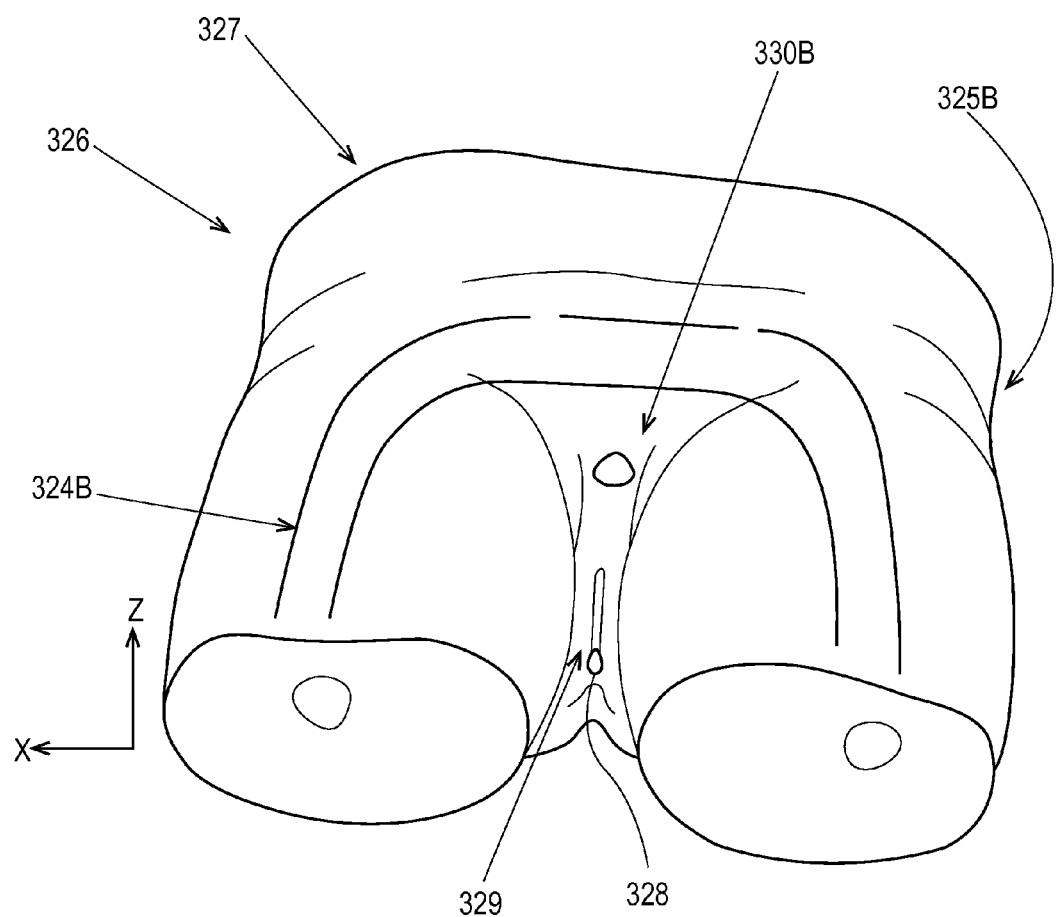
FIG. 3B is a view illustrating a computer based model representing a portion of a female human body.

FIG. 3B is a view illustrating a computer based model 326 that represents a portion of a female human body 327. The female human body 327 includes a support structure 324B, a flesh structure 325B, a female pee point 328, an anus 330B, and a vaginal opening 329. The female pee point 328 is located in an anatomically correct location, which is the urethral opening in the center of the pudendal region. The vaginal opening 329 is also located in an anatomically correct location, which is at the rear of the pudendal region. The anus 330B is located in an anatomically correct location, in the rear beyond the pudendal region. The support structure 324B is generally configured in a manner similar to the like-numbered element in FIG. 3A. The flesh structure 325A provides an approximation of the skin, tissue, muscle, and organs of a female human body, and is otherwise generally configured in a manner similar to the like-numbered FIG. 3A. The female human body 327 can be constrained to assume one or more particular positions or to assume a change in position, in the same way as the male human body 322.

Each of the computer based models 321 and 326 can represent a human body of any age, including, for example: as an infant, a toddler, a child, an adolescent, a young adult, a middle-aged adult, an older adult, or an elderly person. Each of the computer based models 321 and 326 can represent a human of any body type, including, variations in size and shape.

Each of the computer based models 321 and 326 can be created as described below, with general references to a computer based model of a human body. A computer based model that represents a human body can be created by providing dimensions and material properties to modeling software and by generating a mesh for the article using meshing software.

A computer based model of a human body can be created with dimensions that are similar to or the same as dimensions of one or more real world human bodies. These dimensions can be determined by measuring bodies, by using known values, or by estimating values. The model can be created by putting values for dimensions of the human body into the modeling software.

The computer based model of the human body can be created with material properties that are similar to or the same as material properties that represent a real world human body. These material properties can be determined by measuring actual samples, by using known values, or by estimating values.

The computer based model of the human body can be created with a mesh for the parts of the body. A support structure of a human body can be created by using shell elements, such as S3R, defined as rigid element sets, with an element size of about 0.1 mm to about 10 mm, about 1 mm to about 8 mm such as, for example, 0.5 mm, 2 mm, 3 mm, 4 mm, 5 mm, 6 mm, 6.5 mm, 7 mm, 7.5 mm, 8 mm, 8.5 mm, 9 mm. Also, a flesh structure of a human body can be created by using deformable, solid elements, such as C3D4 with an element size of about about 0.1 mm to about 10 mm, about 1 mm to about 8 mm such as, for example, 0.5 mm, 2 mm, 3 mm, 4 mm, 5 mm, 6 mm, 6.5 mm, 7 mm, 7.5 mm, 8 mm, 8.5 mm, 9 mm.

Figure 4A:
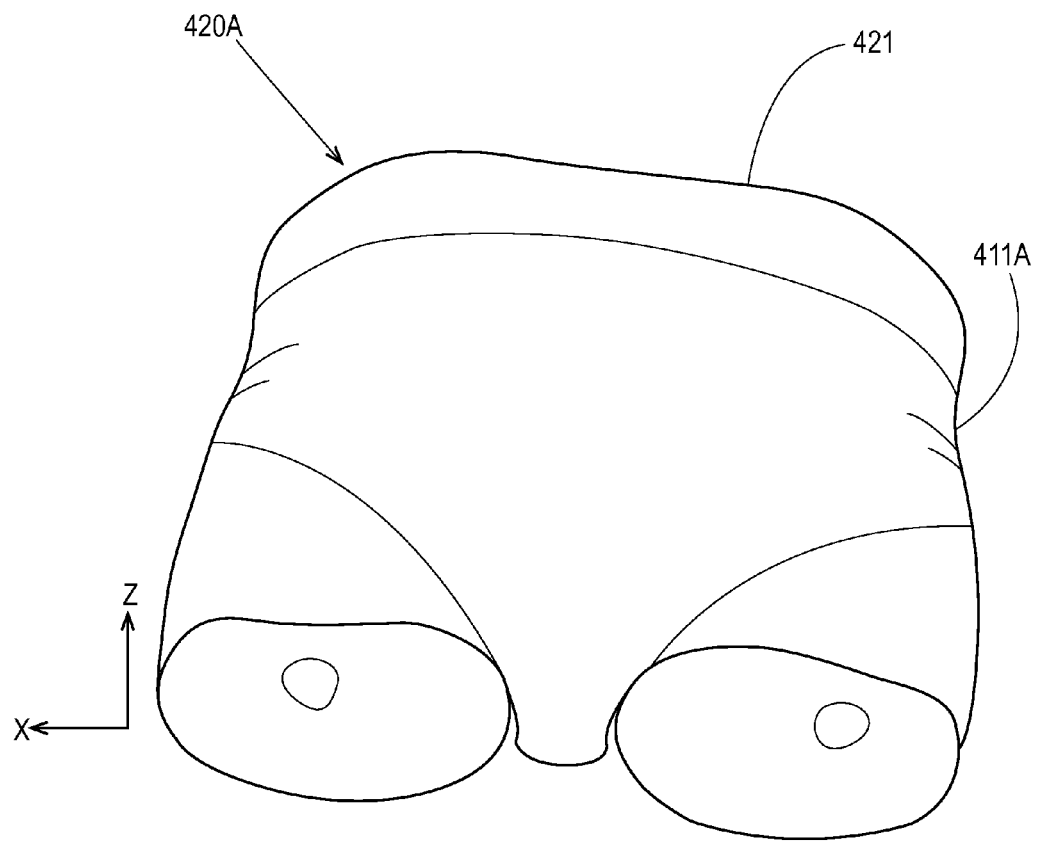
FIG. 4A is a bottom view illustrating a computer based model representing a pant-type wearable absorbent article fitted to a portion of a male human body.

FIG. 4A is a bottom view illustrating a computer based model 420A representing a pant-type wearable absorbent article 411A fitted to a portion of a male human body 421. The model of the male human body 421 can be configured in the same way as the model 321 of FIG. 3A. A computer based model can represent a pant-type wearable absorbent article fitted to a portion of a female human body, wherein the model of the female human body can be configured in the same way as the model 326 of FIG. 3B. The model 420A may also include one or more garments worn by the human body.

Figure 4B:
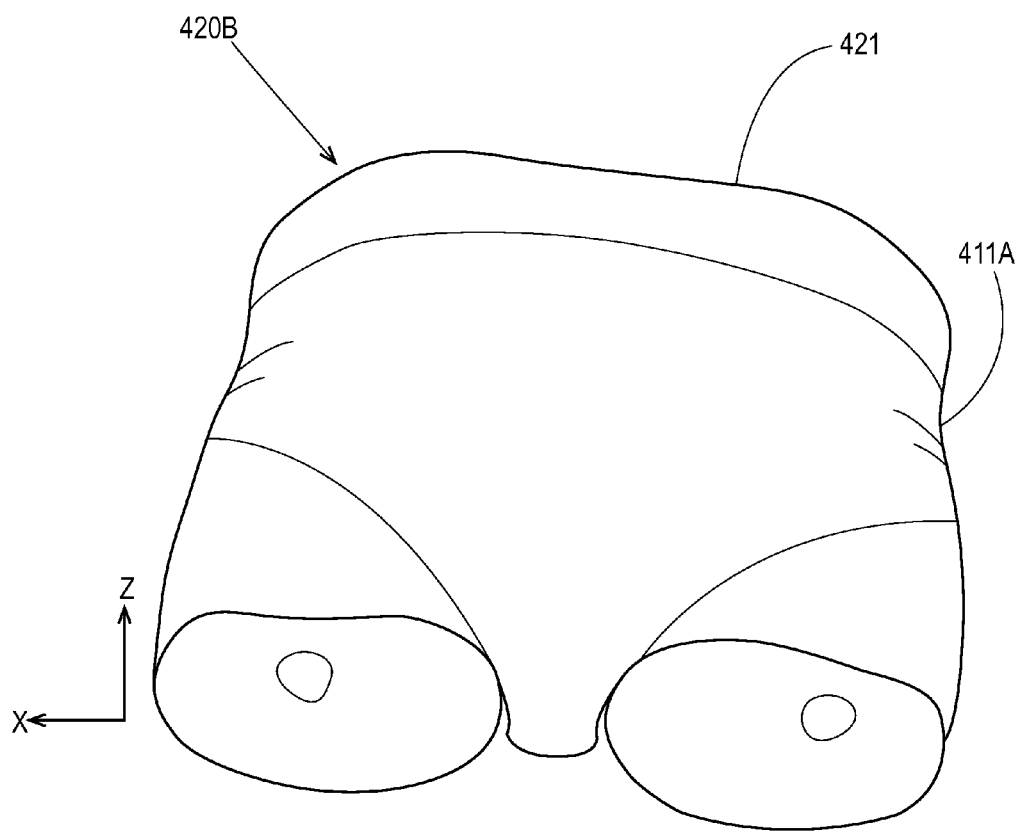
FIG. 4B is a bottom view illustrating a computer based model representing a pant-type wearable absorbent article fitted to a portion of a female human body.

FIG. 4B is a front view illustrating a computer based model 420B representing a pant-type wearable absorbent article 411A fitted to a portion of a female human body 426. The model of the female human body 426 can be configured in the same way as the model 326 of FIG. 3B. A computer based model can represent a pant-type wearable absorbent article fitted to a portion of a male human body, wherein the model of the male human body can be configured in the same way as the model 321 of FIG. 3A. The model 420B may also include one or more garments worn by the human body.

Each of the computer based models 420A and 420B can be created as described below, with general references to computer based models of wearable absorbent articles and human bodies. In a computer based model, a model of a human body can don a model of a wearable absorbent article in various ways. As a first example, a model of a wearable absorbent article can be positioned and/or constrained to represent the absorbent article as if it is being fitted to a human body, and the model of the human body can then be positioned inside of the wearable absorbent article.

As a second example, a model of a wearable absorbent article can be fitted to a model of a human body in a manner that is similar to or the same as real-world movements of a human body donning a wearable absorbent article. As an example, for a pant-type wearable absorbent article, the fitting may include rotating the legs of the human body and fastening the article around the lower torso of the body. As another example, for a pant-type wearable absorbent article, the fitting may include spreading the legs of the human body and pulling the article up unto the lower torso of the body.

Figure 4C:
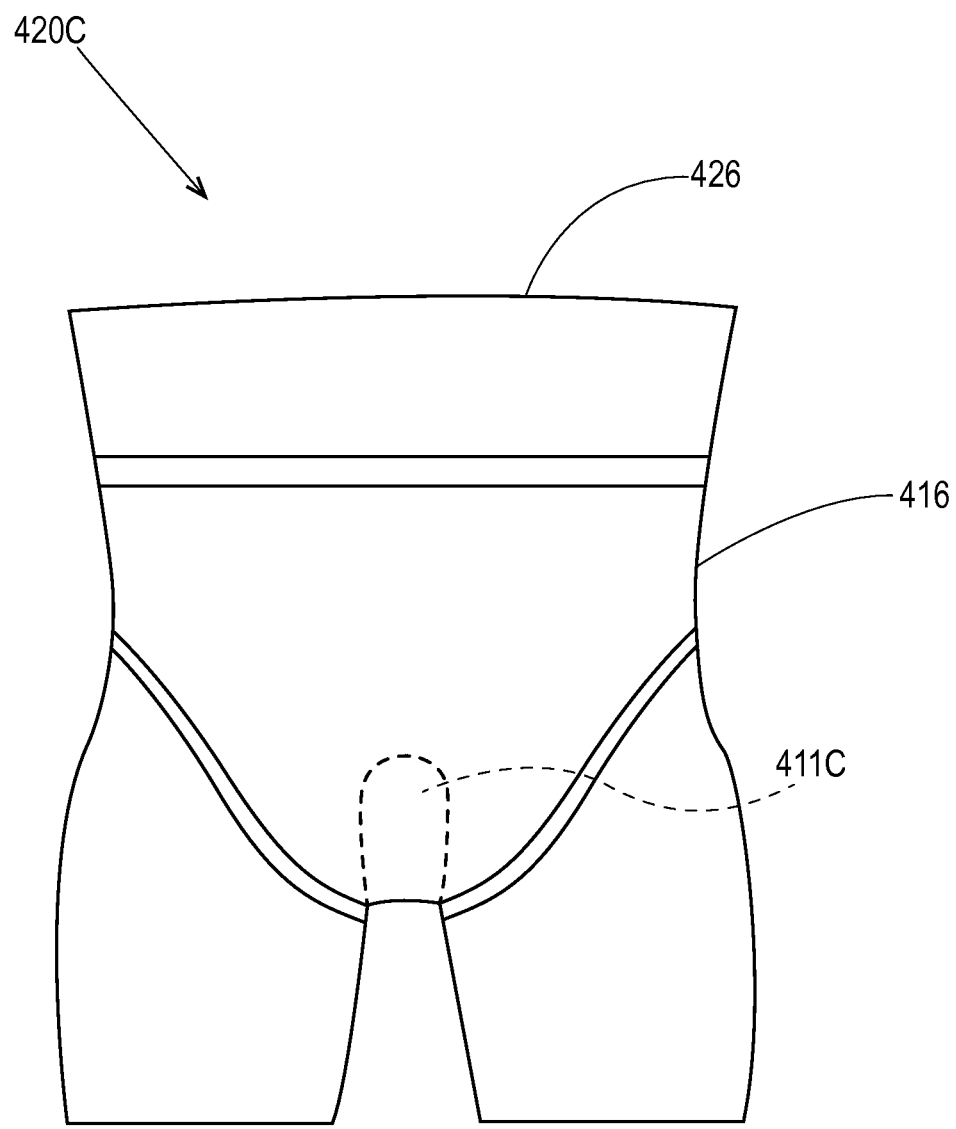
FIG. 4C is a bottom view illustrating a computer based model representing a feminine pad absorbent article fitted to a portion of a female human body.

FIG. 4C is a front view illustrating a computer based model 420C representing a feminine pad absorbent article 411C fitted to a portion of a female human body 426 inside of a garment 416 worn by the female human body 426. The model of the female human body 426 can be configured in the same way as the model 326 of FIG. 3B. In FIG. 4C, the garment 416 is holding the feminine pad absorbent article 411A in an in-use position.

The garment 416 can be any kind of garment, such as an undergarment. A computer based model that represents a garment can be created by providing appropriate dimensions and material properties to modeling software and by generating a mesh for the garment using meshing software. The model 420C may also include one or more additional garments worn by the human body.

The computer based model 420C can be created as described below, with general references to computer based models of feminine absorbent articles and human bodies. In a computer based model, a model of a feminine wearable absorbent article can be placed in an in-use position for a model of a human body in various ways. A model of a feminine absorbent article can be fitted to a model of a human body in a manner that is similar to or the same as real-world movements of a human body placing the article in an in-use position. As an example, a model of a garment can be positioned and/or constrained to represent the garment as if it is being fitted to a human body, a model of a feminine wearable absorbent article can be positioned and/or constrained to represent the article as if it is being held by the garment, and the model of the human body can then be positioned inside of the garment.

The garment 416 can be omitted and the model 420C can be modified, to simulate a fitting of the absorbent article to a human body without using a garment. Boundary conditions can position and/or constrain the model of the feminine pad absorbent article 411A to represent the feminine pad absorbent article 411A as if it is being fitted to a human body. While this alternate approach may not form a completely realistic representation of the fitted absorbent article, it may still be used to provide some of the benefits of the model.

Each of the computer based models 420A, 420B, and 420C can be created as described below, with general references to computer based models of absorbent articles, garments, and human bodies. In a computer based model, the fitting of an absorbent article to a human body may represent an ideal fit as intended by the manufacturer of the absorbent article, or the fitting may represent a less than ideal fit as sometimes occurs in the real-world use of absorbent articles. Additionally, a computer based model can represent the removal of an absorbent article from a human body, in various ways. These approaches can be accomplished with the use of boundary conditions in the models, as will be understood by one of skill in the art.

A computer based model that represents a human body and an absorbent article can also include a representation of part, or parts, or all of one or more environmental objects and/or one or more environmental conditions. An environmental object can be any object that would physically interact with an absorbent article or a human body in the real-world. For example, an environmental object can be a changing surface, on which a human body is placed when fitting an absorbent article to the body. An environmental condition can be any condition that would physically interact with an absorbent article or a human body in the real-world. As examples, an environmental condition can be gravity, hot or cold temperatures, etc.

A computer based model that represents a human body and an absorbent article can include defined interactions between its parts. Defined interactions are prescribed terms that govern physical relationships within a computer based model. Examples of defined interactions include terms that govern the presence, absence, or magnitude of contact, friction, relative movement, and other physical relationships. Each defined interaction can be assigned a particular value and extent within the model.

These interactions can be determined by observing, measuring, analyzing, and/or estimating real world physical interactions. Computer based models can also include one or more defined interactions that differ from real world physical interactions, in order to account for inherent limitations in the models and/or to more accurately represent the overall physical behaviors of real world things, as will be understood by one of ordinary skill in the art. Defined interactions can act on the model in various ways, to allow, prohibit, amplify, or limit one or more physical relationships in the model.

Each of the models 420A, 420B, and 420C includes defined interactions that allow part, or parts, or all of the human body to physically interact with part, or parts, or all of the absorbent article. When a model includes a garment, the model can include defined interactions that allow part, or parts, or all of the garment to physically interact with part, or parts, or all of the absorbent article, and/or to physically interact with part, or parts, or all of the human body. When a model includes environmental objects or conditions, the model can include defined interactions that allow part, or parts, or all of the environmental objects or conditions to physically interact with part, or parts, or all of the absorbent article, and/or to physically interact with part, or parts, or all of the human body.

Figure 5:
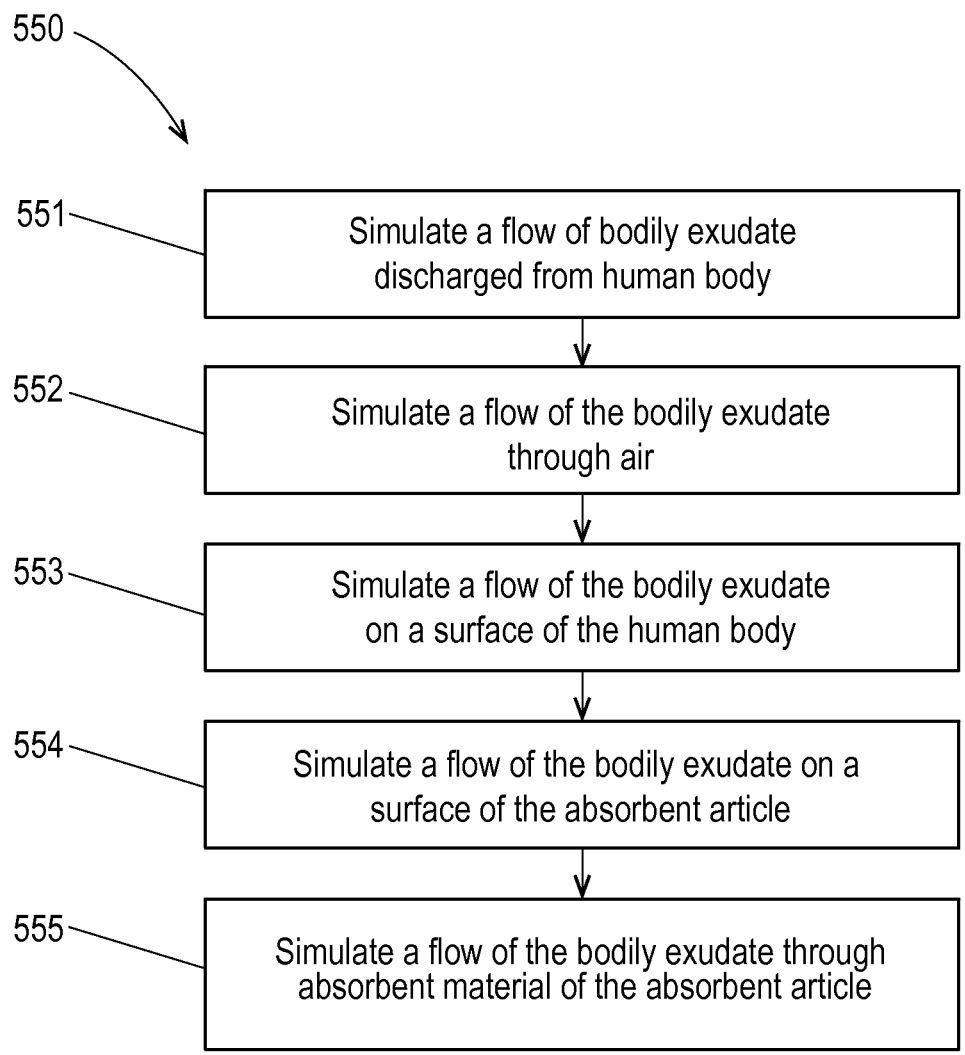
FIG. 5 is a chart illustrating a method of using computer based models for simulating the discharge and flow of a bodily exudate in an absorbent article.

FIG. 5 is a chart illustrating a method 550 of using computer based models for simulating the discharge and flow of a bodily exudate in an absorbent article. Part, or parts, or all of the method 550 can be used in the fifth step 150 of the method 100 of FIG. 1. Accordingly, in the description of the method 550, a reference to an absorbent article refers to a computer based model of an absorbent article, as described in connection with the first step 110 and the third step 130 of the method 100 of FIG. 1, and a reference to a human body refers to a computer based model of a human body, as described in connection with the second step 120 and the third step 130 of the method 100 of FIG. 1. The steps of the method 550 are also explained in relation to FIGS. 6A-6C, as described below. Although the steps 551-555 are described in numerical order in the present disclosure, some or all of these steps can be performed in other orders, and/or at overlapping times, and/or at the same time, as will be understood by one of ordinary skill in the art.

Figure 6A:
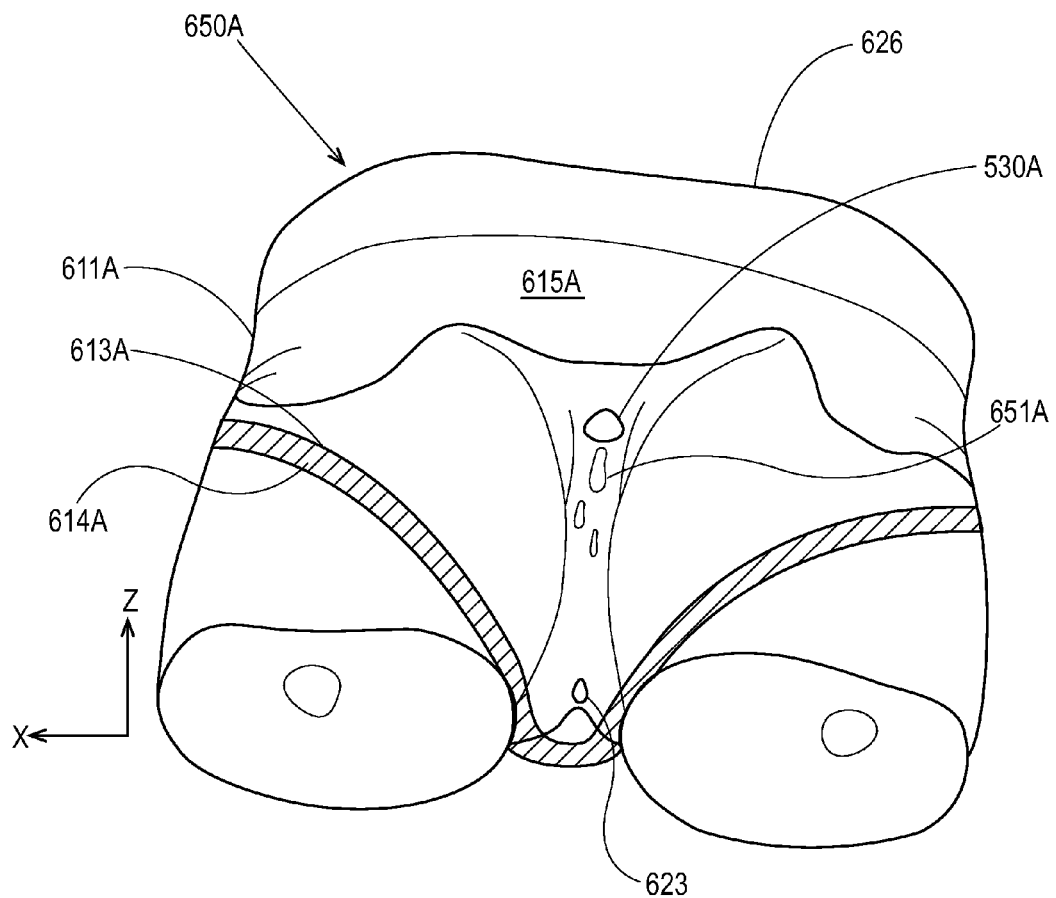
FIG. 6A is a bottom view illustrating a computer based model simulating a feces discharge from a male human body to a wearable absorbent article.
Figure 6B:
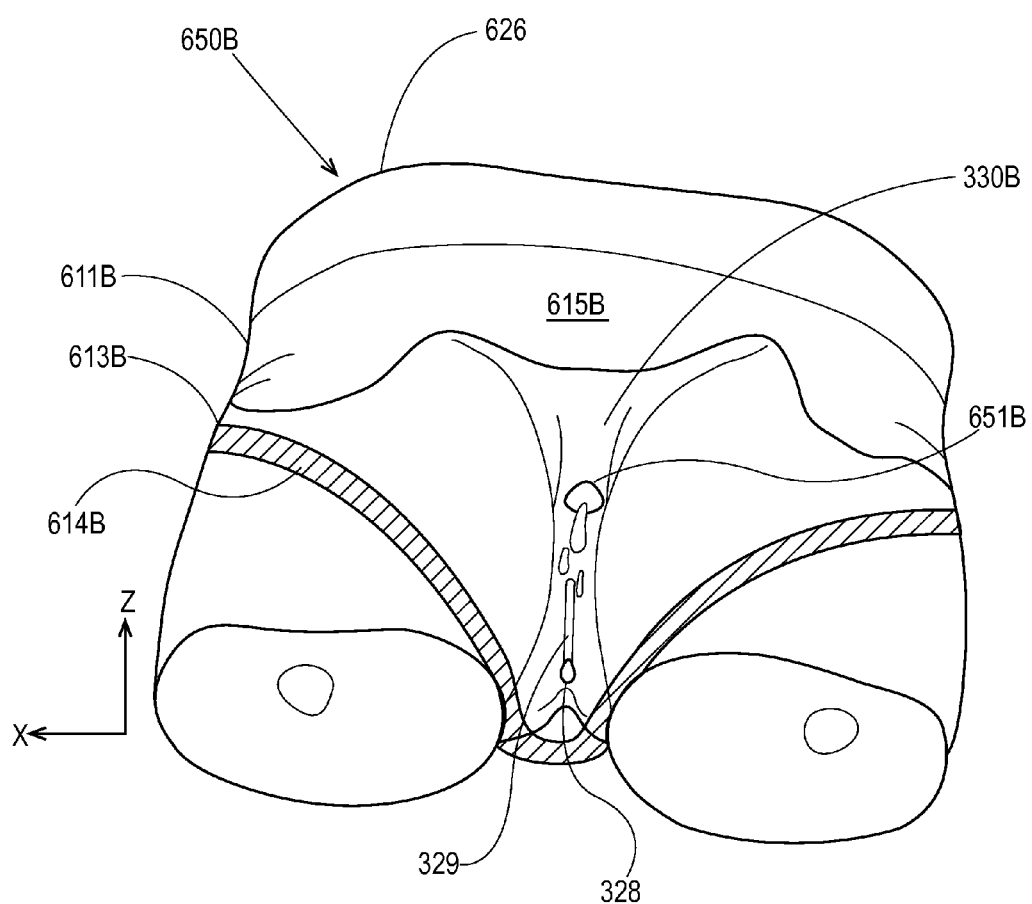
FIG. 6B is a bottom view illustrating a computer based model simulating a feces discharge from a female human body to a wearable absorbent article.
Figure 6C:
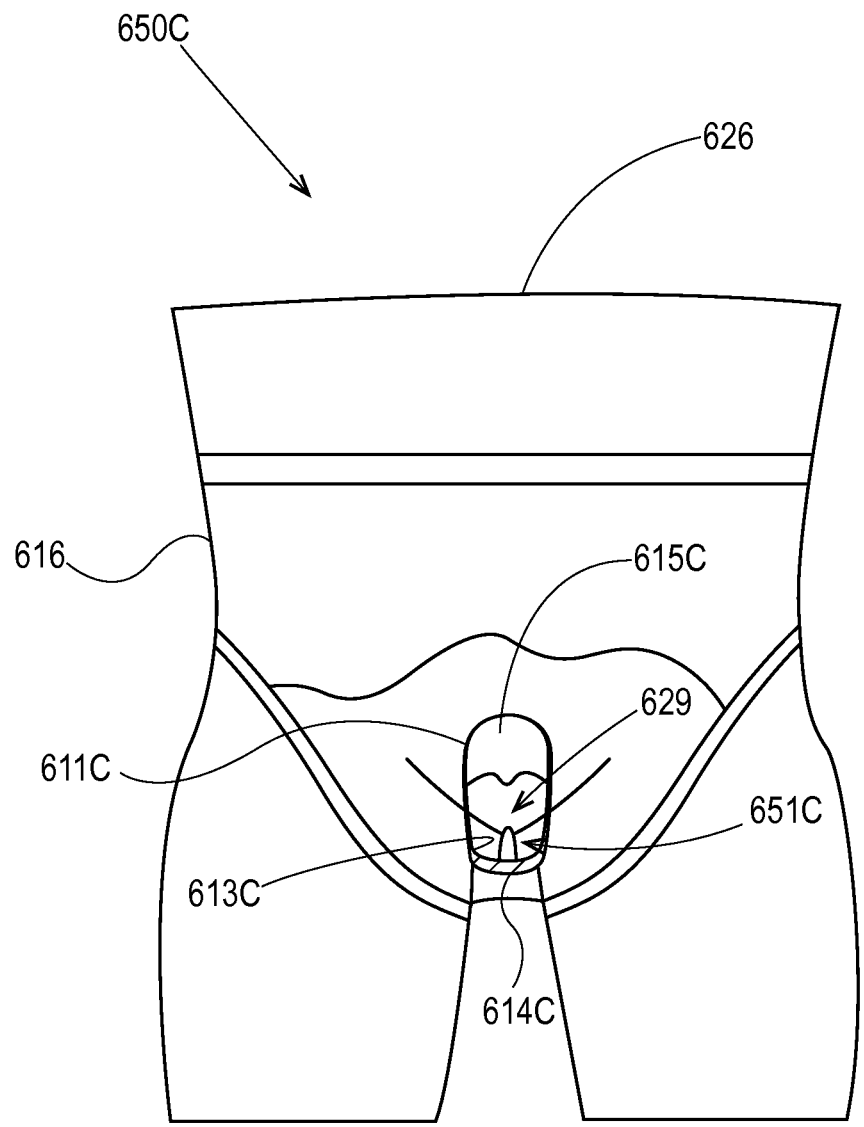
FIG. 6C is a front view illustrating another computer based model simulating a menses discharge from a female human body to a feminine absorbent article.

The method 550 includes a first step 551 of simulating a flow of bodily exudate as it is discharged from the human body. The discharge in the first step 551 can simulate a discharge of feces from a male human body, as illustrated in FIG. 6A, a discharge of feces from a female human body, as illustrated in FIG. 6B, a discharge of menses from a female human body, as illustrated in FIG. 6C, or a discharge of any kind of bodily exudate from a male human body, a female human body, or an androgynous human body. The discharge in the first step 551 can simulate more than one exudate discharge simultaneously, such as, for example, feces and urine simultaneously.

A computer based model that represents a bodily exudate can be created by providing volume and material properties to modeling software and by generating a mesh for the exudate using meshing software. A computer based model of a bodily exudate can be created with a volume that is similar to or the same as a volume of one or more discharges from real world human bodies. These volumes can be determined by measuring discharges of bodily exudates, by using known values, or by estimating values. The model can be created by putting values for a volume of the bodily exudate into the modeling software. The computer based model of the human body can be created with exudate properties that are similar to or the same as exudate properties that represent a real world bodily exudate. These material properties can be determined by measuring actual samples, by using known values, or by estimating values.

In general, urine can be modeled as a non-viscous or Newtonian viscous exudate, similar to water. In general, feces can be modeled as viscous or Non-Newtonian exudates. Feces may also be modeled as a mixture of Newtonian and Non-Newtonian exudates. A model of a bodily exudate can be created by using structured mesh cells, such as finite volumes with a cell size of about 0.1 mm to about 2 mm, about 0.5 mm to about 1 mm such as, for example, about 0.2 mm, about 0.3 mm, about 0.4 mm, about 0.5 mm, about 0.6 mm, about 0.7 mm, about 0.8 mm, about 0.9 mm, about 1.1 mm, about 1.2 mm, about 1.3 mm, about 1.4 mm, about 1.5 mm, about 1.6 mm, about 1.7 mm, about 1.8 mm, about 1.9 mm, to represent urine. Menses and feces can have varying consistencies, which can be modeled in various ways, as a viscous or non-viscous exudate, having Newtonian or Non-Newtonian properties. A model of a bodily exudate can be created by using structured mesh cells, such as finite volumes with a cell size of about 0.1 mm to about 2 mm, about 0.5 mm to about 1 mm such as, for example, about 0.2 mm, about 0.3 mm, about 0.4 mm, about 0.5 mm, about 0.6 mm, about 0.7 mm, about 0.8 mm, about 0.9 mm, about 1.1 mm, about 1.2 mm, about 1.3 mm, about 1.4 mm, about 1.5 mm, about 1.6 mm, about 1.7 mm, about 1.8 mm, about 1.9 mm, to represent menses and/or feces.

If the model of the human body is androgynous, then the location and orientation of the discharge of the model of the bodily exudate can be approximated with reference to the human body. For example, the discharge may be provided from a front or central portion of an outside of a crotch of the model of the androgynous human body. Similarly to the method 500, wherein a model of a human body is not used, the location and orientation of the discharge of the model of the bodily exudate may be approximated with reference to the model of the absorbent article. For example, the discharge may be provided to a front or central portion of an inside of a crotch of the model of the absorbent article.

The method 550 includes a second step 552 of simulating a flow of the model of bodily exudates through a model of air within the domain. A computer based model that represents air can be created by providing dimensions and air properties to modeling software and by generating a mesh for the air using meshing software. The second step 552 can be omitted, and the model of the bodily exudate can be provided to the model of the absorbent article without simulating a movement through air.

The method 550 includes a third step 553 of simulating a flow of the model of bodily exudate on a surface of the model of the human body. The third step 553 can be omitted, and the model of the bodily exudate can be provided to the model of the absorbent article without simulating a flow of the model of bodily exudate on a surface of the model of the human body.

The method 550 also includes a fourth step 554 of simulating a flow of the model of bodily exudate on a surface of the model of the substrate.

The method 550 can also include a fifth step 555 of simulating a flow of the model of bodily exudate through absorbent material of the absorbent article.

FIG. 6A is a bottom view illustrating a computer based model 650A simulating a feces discharge 651A from a portion of a male human body 621 to a pant-type wearable absorbent article 611A that is fitted to the male human body 621. The model 650A is configured in the same way as the model 420A of FIG. 4A.

The pant-type wearable absorbent article 611A includes a wearer-facing external surface 613A, an absorbent material 614A, and a garment-facing external surface 615A, which are each configured in the same manner as the like-numbered element in FIG. 2B. The male human body 621 includes a male pee point 623, which is configured in the same manner as the like-numbered element in FIG. 3A.

In FIG. 6A, the feces discharge 651A originates from the male anus point 330A and flows through air to the wearer-facing external surface 613A of the pant-type absorbent article 611A. The feces then flows on and/or through the wearer-facing external surface 613A, as well as into and/or through the absorbent material 614A. As part of the simulating, feces may also flow on an external surface of the male human body 621. CFD program instructions can execute to simulate each of these exudate flows.

FIG. 6B is a bottom view illustrating a computer based model 650B simulating a feces discharge 651B from a female human body 626 to a pant-type wearable absorbent article 611A that is fitted to the female human body 626. The model 650B is configured in the same way as the model 420B of FIG. 4B.

The pant-type wearable absorbent article 611A includes a wearer-facing external surface 613A, an absorbent material 614A, and a garment-facing external surface 615A, which are each configured in the same manner as the like-numbered element in FIG. 2A. The female human body 626 includes a female pee point 628, which is configured in the same manner as the like-numbered element in FIG. 3B.

In FIG. 6B, the feces discharge 651B originates from the female anus point 330B and flows on an external surface of the female human body 626 and/or through air to the wearer-facing external surface 613A of the pant-type absorbent article 611A. The urine then flows on and/or through the wearer-facing external surface 613A, as well as into and/or through the absorbent material 614A. CFD program instructions can execute to simulate each of these exudate flows.

FIG. 6C is a front view illustrating a computer based model 650C simulating a menses discharge 651C from a female human body 626 to a feminine pad wearable absorbent article 611C that is inside of a garment 616 and fitted to the female human body 626. The model 650C is configured in the same way as the model 420C of FIG. 4C.

The feminine pad wearable absorbent article 611C includes a wearer-facing external surface 613C, an absorbent material 614C, and a garment-facing external surface 615C, which are each configured in the same manner as the like-numbered element in FIG. 2C. The female human body 626 includes a vaginal opening 629, which is configured in the same manner as the like-numbered element in FIG. 3B. The garment 616 is configured in the same manner as the like-numbered element in FIG. 4C.

In FIG. 6C, the menses discharge 651C originates from the female vaginal opening 629 and flows on an external surface of the female human body 626 and/or through air to the wearer-facing external surface 613C of the feminine pad absorbent article 611C. The menses then flows on and/or through the wearer-facing external surface 613C, as well as into and/or through the absorbent material 614C. CFD program instructions can execute to simulate each of these exudate flows.

Figure 7:
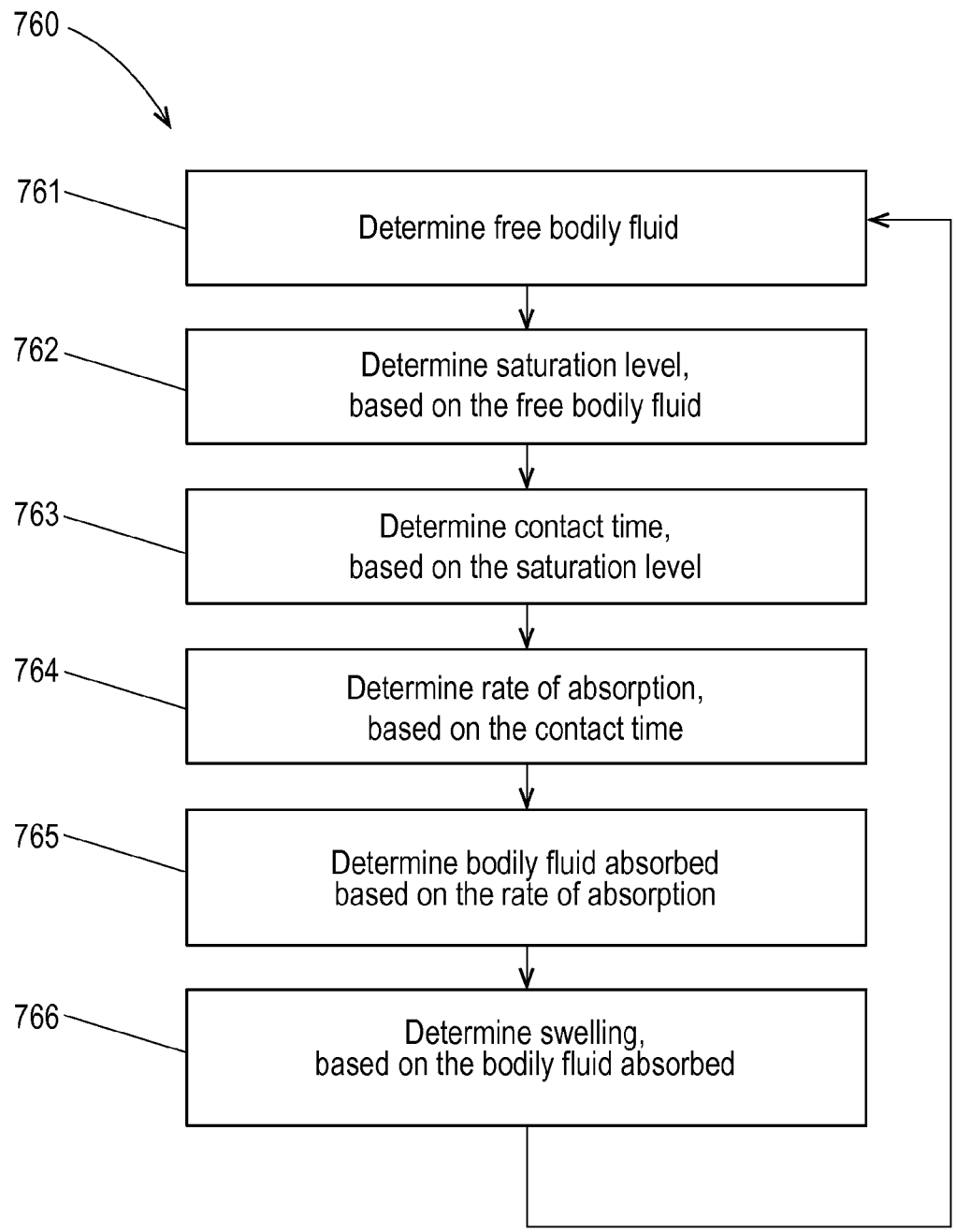
FIG. 7 is a chart illustrating a method of using computer based models for determining swelling from a bodily fluid in an absorbent article.

FIG. 7 is a chart illustrating a method 760 of using computer based models for determining a swelling of an absorbent material in an absorbent article from a provision of a bodily fluid. Accordingly, in the description of the method 760, a reference to an absorbent article refers to a computer based model of an absorbent article, and a reference to a human body refers to a computer based model of a human body, as described in connection with the method 100 of the embodiment of FIG. 1. Further, in the description of the method 760, a reference to an element refers to an exemplary element in a set of discrete elements, wherein each element represents a volume including absorbent material of the absorbent article.

The method 760 is intended to be performed in an iterative fashion. Each iteration of the method 760 is performed in a particular time step, which governs the time-dependent physical behavior of the bodily fluid and the absorbent material. The method 760 is also intended to be performed for each element in the set of discrete elements. Although the steps 761-766 are described in numerical order in the present disclosure, in various embodiments some or all of these steps can be performed in other orders, and/or at overlapping times, and/or at the same time, as will be understood by one of ordinary skill in the art.

The method 760 includes a first step 761 of determining an amount of free bodily fluid currently in the element. As used herein, the term free bodily fluid refers to a bodily fluid that is not absorbed within an absorbent material, but is free to move in, on, or through the absorbent article or be absorbed by the absorbent material. The amount of free bodily fluid currently in the element can be determined based on the amount of free bodily fluid previously in the element, the amount of the bodily fluid previously absorbed by absorbent material in the element, the amount of the bodily fluid flowing into the element, and the amount of the bodily fluid flowing out of the element. This relationship can be expressed as follows:

$$M_{free\,fluid\,curr} = M_{free\,fluid\,pre} - M_{fluid\,abs\,prev} + M_{fluid\,in} - M_{fluid\,out}$$

Each of these variables can be expressed as a value in grams, or another appropriate unit of mass. In an alternate embodiment, these variables can be expressed in units of volume.

$M_{free\,fluid\,prev}$ represents the mass of the free bodily fluid in the element, at the beginning of the first step 761. In an initial iteration of the method 760, a value for $M_{free\,fluid\,prev}$ can be determined from a simulated provision of bodily fluid to the element. The provision of a free bodily fluid can be simulated as described in connection with the fifth step 150 of the method 100 of the embodiment of FIG. 1. Alternatively, the provision can be simulated by another computer based model of a free bodily fluid, as described herein or as known to one of skill in the art. When the method 760 is performed in an iterative fashion, $M_{free\ fluid\ curr}$ from a first iteration of the method can be used as $M_{free\ fluid\ prev}$ in a second iteration of the method.

$M_{fluid\ abs\ prev}$ represents the mass of the bodily fluid previously absorbed by the absorbent material in the element. In an initial iteration of the method 760, a value for $M_{fluid\ abs}$ can be set to zero. When the method 760 is performed in an iterative fashion, $M_{fluid\ abs\ curr}$ from the fifth step 765 of a first iteration of the method can be used as $M_{fluid\ abs\ prev}$ in the first step 761 of a second iteration of the method. Alternatively, $M_{fluid\ abs\ prev}$ can be determined by another computer based model of absorption, as described herein or as known to one of skill in the art.

$M_{fluid\ in}$ represents the mass of the bodily fluid flowing into the element, during the first step 761. $M_{fluid\ out}$ represents the mass of the bodily fluid flowing out of the element, during the first step 761. The bodily fluid can flow into and out of the element. $M_{fluid\ in}$ and $M_{fluid\ out}$ can be determined by using fluid dynamics. Program instructions, such as CFD program instructions, can execute to use fluid dynamics to determine the flow of the bodily fluid into and out of the element.

$M_{free\ fluid\ curr}$ represents the calculated mass of the free bodily fluid in the element, at the end of the first step 761. Program instructions can execute to calculate $M_{free\ fluid\ curr}$ from the equation shown above. In an alternate embodiment of the method 760, the first step 761 can be omitted and $M_{free\ fluid\ curr}$ can be determined by another computer based model of free bodily fluid in an element of absorbent material, as described herein or as known to one of skill in the art. For example, models for simulating the physical behavior of bodily fluids with absorbent articles can be found in US patent application publication 2009/0099793, "Method for Evaluation of Absorption Behavior of Absorbent Articles" by Rosati, et al.

The method 760 includes a second step 762 of determining a current saturation level of the bodily fluid in the element. The current saturation level in the element can be determined based on the amount of free bodily fluid in the element, the density of the bodily fluid, the porosity of the absorbent material in the element, and the volume of the element. This relationship can be expressed as follows:

$$S_{elementcurr} = \frac{M_{freefluidcurr}}{(\rho_{fluid})(\varepsilon_{abs})(\Omega_{elementcurr})}$$

$M_{free\ fluid\ curr}$ represents the mass of the free bodily fluid in the element during the second step 762. $M_{free\ fluid\ curr}$ can be determined as described in connection with the first step 761.

$\rho_{fluid}$ represents the density of the bodily fluid and is expressed in grams/cubic centimeter, or other appropriate units of density. $\rho_{fluid}$ can be determined by measuring actual samples, by using known values, or by estimating values for the density of the bodily fluid. In some embodiments, the density of water can be used as an approximate value for the density of urine. In other embodiments, a density of 1.04 grams/cubic centimeter can be used as an estimated value for the density of menses. In the embodiment of FIG. 7, $\rho_{fluid}$ is a constant value.

$\varepsilon_{abs}$ represents a porosity of the absorbent material, during the second step 762. Porosity is the degree to which the absorbent material occupies the element. $\varepsilon_{abs}$ is a unitless value. An $\varepsilon_{abs}$ value of 1.0 represents a complete absence of absorbent material from the element. An $\varepsilon_{abs}$ value of 0.0 represents a presence of absorbent material throughout the entire element. $\varepsilon_{abs}$ can be determined from the model of the absorbent article, as described in connection with the step 110 of the method 100 of the embodiment of FIG. 1. Program instructions can execute to calculate $\varepsilon_{abs}$ based on the amount of the absorbent material in the element and the geometry of the element. Alternatively, $\varepsilon_{abs}$ can be determined by measuring actual samples, by using known values, or by estimating values for the porosity of the absorbent material.

$\Omega_{element\ curr}$ represents the volume of the element, during the second step 762. $\Omega_{element\ curr}$ is expressed in cubic centimeters, or other appropriate units of volume. In an initial iteration of the method 760, $\Omega_{element\ curr}$ can be determined from the model of the absorbent article, as described in connection with the first step 110 of the method 100 of the embodiment of FIG. 1. Program instructions can execute to calculate $\Omega_{element\ curr}$ based on the geometry of the element. When the method 760 is performed in an iterative fashion, $\Omega_{element\ next}$ from the sixth step 766 of a first iteration of the method can be used as $\Omega_{element\ curr}$ in the second step 762 of a second iteration of the method.

$S_{element\ curr}$ represents the current saturation of the element by the free bodily fluid, at the end of the second step 762. $S_{element\ curr}$ is a unitless value. Program instructions can execute to calculate $S_{element\ curr}$ from the equation shown above.

In one alternate embodiment of the method 760, the second step 762 can be omitted and $S_{element\ curr}$ can be determined by another computer based model of saturation, as described herein or as known to one of skill in the art. In other alternate embodiments of the method 760, the second step 762 can be omitted and $S_{element\ curr}$ can be determined by measuring actual samples, by using known values, or by estimating values for the saturation of the element.

The method 760 includes a third step 763 of determining a contact time between the bodily fluid in the element and the absorbent material in the element. The contact time in the element can be determined based on the saturation of the absorbent material in the element. This relationship can be expressed as follows:

$$t_{contactcurr} = \int_0^{t_{current}} S_{element} dt$$

$S_{element}$ represents the saturation of the element by the free bodily fluid over time, from the beginning of the first iteration of the method 760 (t=0) to the third step 763 of the current iteration of the method 760. $S_{element}$ can be determined by plotting $S_{element\ curr}$ versus real world time for each iteration of the method 760. $S_{element\ curr}$ can be determined for each iteration as described in connection with the second step 762.

$t_{current}$ represents the total real world time elapsed from the beginning of the first iteration of the method 760 to the third step 763 of the current iteration of the method 760. $t_{current}$ is expressed as a value in seconds, or another appropriate unit of time. Program instructions can execute to calculate $t_{current}$ by summing up the time values for each of the previous iterations.

$t_{contact\ curr}$ represents the current contact time between the bodily fluid in the element and the absorbent material in the element. $t_{contact\ curr}$ is expressed as a value in seconds, or another appropriate unit of time. Program instructions can execute to calculate $t_{contact\ curr}$ from the relationship shown above, by integrating $S_{element}$ over time, from the beginning of the first iteration of the method 760 (t=0) to $t_{current}$, as will be understood by one of skill in the art. In other words, $t_{contact\,curr}$ can be calculated by summing up the $S_{element\,curr}$ values for each of the iterations.

In one alternate embodiment of the method 760, the third step 763 can be omitted and $t_{contact\,curr}$ can be determined by another computer based model of contact time, as described herein or as known to one of skill in the art. In other alternate embodiments of the method 760, the third step 763 can be omitted and $t_{contact\,curr}$ can be determined by measuring actual samples, by using known values, or by estimating values for the contact time within the element.

The method 760 includes a fourth step 764 of determining a current rate of absorption for the absorbent material in the element. The current rate of absorption can be determined based on the mass of the bodily fluid absorbed by the absorbent material in the element current, which can be determined as a function of the current contact time between the bodily fluid in the element and the absorbent material in the element. This relationship can be expressed as follows:

$$\dot{M}_{fluidabscurr} = \frac{dM_{fluidabs}}{dt} = f(t_{contactcurr})$$

$M_{fluidabs}$ represents the mass of the bodily fluid absorbed over contact time, from the beginning of the first iteration of the method 760 ($t_{contact}=0$) to the fourth step 764 of the current iteration of the method 760. $M_{fluidabs}$ can be determined by plotting $M_{fluidabscurr}$ versus $t_{contact\,curr}$ for each iteration of the method 760. $M_{fluidabscurr}$ can be determined for each iteration as described in connection with the fifth step 765. $t_{contact\,curr}$ can be determined for each iteration as described in connection with the third step 763.

$\dot{M}_{fluidabscurr}$ represents the current mass flow rate for the absorption of the bodily fluid by the absorbent material in the element. $\dot{M}_{fluidabscurr}$ can be expressed as a value in grams per second, or another appropriate unit of mass over time. In alternate embodiments, the absorption flow rate can be expressed in other units. Program instructions can execute to calculate $\dot{M}_{fluidabscurr}$ from the relationship shown above by taking the differential of $M_{fluidabs}$ with respect to time and determining $\dot{M}_{fluidabscurr}$ at the current contact time as will be understood by one of skill in the art. In other words $\dot{M}_{fluidabscurr}$ can be calculated by determining the rate of change for the plot of $M_{fluidabs}$ at $t_{contact\,curr}$.

The method 760 includes a fifth step 765 of determining a current amount of the bodily fluid that is absorbed by the absorbent material in the element during the fifth step 765 of the current iteration. The current amount of the bodily fluid that is absorbed can be determined based on the current rate of absorption for the absorbent material in the element and the time step for the current iteration. This relationship can be expressed as follows:

$$M_{fluidabscurr}=(\dot{M}_{fluidabscurr} \cdot t_{step})$$

$\dot{M}_{fluidabscurr}$ represents the current mass flow rate for the absorption of the bodily fluid by the absorbent material in the element. $\dot{M}_{fluidabscurr}$ can be determined as described in connection with the fourth step 764. $t_{step}$ represents the time step for the current iteration of the method 760. $M_{fluid\,abs\,curr}$ represents the mass of the bodily fluid absorbed by the absorbent material in the element, during the current iteration. Program instructions can execute to calculate $M_{fluid\,abs\,curr}$ from the equation shown above.

In various embodiments, the amount of the bodily fluid that is absorbed may be limited by the amount of free bodily fluid in the element. That is $M_{free\,fluid\,curr}$ may limit the $M_{fluid\,abs\,curr}$. Program instructions can execute to calculate $M_{fluid\,abs\,curr}$ by taking into account limitations from $M_{free\,fluid\,curr}$.

In one alternate embodiment of the method 760, the fifth step 765 can be omitted and $M_{fluid\,abs\,curr}$ can be determined by another computer based model of the bodily fluid absorbed by the absorbent material, as described herein or as known to one of skill in the art. In other alternate embodiments of the method 760, the fifth step 765 can be omitted and $M_{fluid\,abs\,curr}$ can be determined by measuring actual samples, by using known values, or by estimating values for the bodily fluid absorbed within the element.

The method 760 includes a sixth step 766 of determining a new swollen volume of the element. The new swollen volume of the element can be determined as a function of the total mass of the bodily fluid that has been absorbed by the absorbent material in the element, the porosity of the absorbent material in the element, and the amount of the absorbent material in the element. This relationship can be expressed as follows:

$$\Omega_{element\,next}=f(M_{fluid\,abs\,curr\,tot},\epsilon_{abs},M_{abs\,matl})$$

$M_{fluid\,abs\,curr\,tot}$ represents the total mass of the bodily fluid that has been absorbed by the absorbent material in the element, as of the current iteration. $M_{fluid\,abs\,curr\,tot}$ can be expressed as a value in grams, or another appropriate unit of mass. In an alternate embodiment, the amount of the bodily fluid absorbed in the element can be expressed in units of volume. Program instructions can execute to calculate $M_{fluid\,abs\,curr\,tot}$ by summing up the $M_{fluid\,abs\,curr}$ values for each of the iterations. $\epsilon_{abs}$ represents a porosity of the absorbent material, and can be determined as described in the second step 762. $M_{abs\,matl}$ represents the mass of the absorbent material. $M_{abs\,matl}$ can be expressed as a value in grams, or another appropriate unit of mass. In an alternate embodiment, the amount of the absorbent material in the element can be expressed in units of volume. $\Omega_{element\,next}$ represents the new swollen volume of the element, at the end of the sixth step. $\Omega_{element\,next}$ is expressed in cubic centimeters, or other appropriate units of volume. Program instructions can execute to calculate $\Omega_{element\,next}$ from the relationship shown above, as will be understood by one of skill in the art.

In the relationship shown above $\Omega_{element\,next}$ is a function of the variables $\Omega_{element\,curr}$, $M_{fluid\,abs\,curr}$, $\epsilon_{abs}$, and $M_{abs\,matl}$. This functional relationship can be determined based on empirical results for a particular absorbent material. In alternate embodiments, $\Omega_{element\,next}$ can be expressed as a function of less than all of the variables $M_{fluid\,abs\,curr}$, $\epsilon_{abs}$, and $M_{abs\,matl}$. As a first example, $\Omega_{element\,next}$ can be expressed as a function of $M_{fluid\,abs\,curr}$ and $M_{abs\,matl}$. As a second example, $\Omega_{element\,next}$ can be expressed as a function of $M_{fluid\,abs\,curr}$ and $\epsilon_{abs}$. In various embodiments, $\Omega_{element\,next}$ can also be expressed as a function of one or more other variables describing the physical characteristics of the absorbent material, the bodily fluid, and/or the element, as will be understood by one of skill in the art.

As an example of the functional relationship described above, the new swollen volume of the element can be determined based on the total mass of the bodily fluid that has been absorbed by the absorbent material in the element, the mass of the bodily fluid that has been absorbed per unit of mass of the absorbent material in the element, the density of the absorbent material in the element, and the volume fraction of absorbent material in the element. This relationship can be expressed as follows:

$$\Omega_{elementnext} = \frac{M_{fluidabscurrtot}}{(xload)(\rho_{abs})(f_{abscurr})}$$

$M_{fluid\ abs\ curr\ tot}$ represents the total mass of the bodily fluid that has been absorbed by the absorbent material in the element, as of the current iteration, as described above.

xload represents the mass of the bodily fluid that has been absorbed per unit of mass of the absorbent material in the element, as of the current iteration. xload is a unitless value. xload can be determined by measuring actual samples, by using known values, or by estimating values for the bodily fluid absorbed within the absorbent material in the element. xload can also be determined as a function of the current contact time, based on empirical results for a particular absorbent material.

$\rho_{abs}$ represents the density of the absorbent material and is expressed in grams/cubic centimeter, or other appropriate units of density. $\rho_{abs}$ can be determined by measuring actual samples, by using known values, or by estimating values for the density of the bodily fluid. In the embodiment of FIG. 7, $\rho_{abs}$ is a constant value.

$f_{abscurr}$ represents volume fraction of absorbent material in the element, as of the current iteration. $f_{abscurr}$ is a unitless value. $f_{abscurr}$ can be determined by measuring actual samples, by using known values, or by estimating values for the volume of the absorbent material within the element. $f_{abscurr}$ can also be determined as a function of the porosity of the absorbent material in the element, based on empirical results for a particular absorbent material.

By repeating steps 761-766 in iterative fashion, the swelling of an element of absorbent material can be determined. By applying this method to the elements of the absorbent material, the overall swelling of the absorbent material can be determined and can be applied to a computer based model of the absorbent article, as illustrated in the embodiment of FIGS. 8A-8B.

Figure 8A:
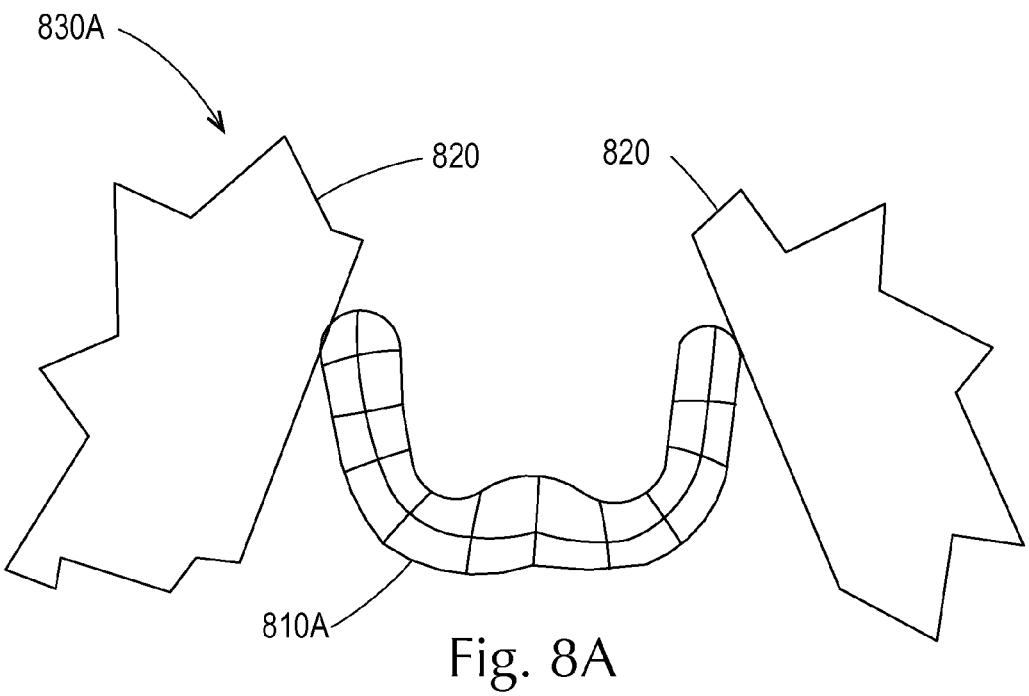
FIG. 8A is a cross-sectional side view illustrating a computer based model of an absorbent article fitted to a portion of a human body, wherein the article is in an unswollen state.

FIG. 8A is a cross-sectional side view illustrating a computer based model 830A of an absorbent article 810A fitted to a portion of a human body 820, wherein the article 810A is in an unswollen state, as in the third step 130 of the method 100 of the embodiment of FIG. 1.

Figure 8B:
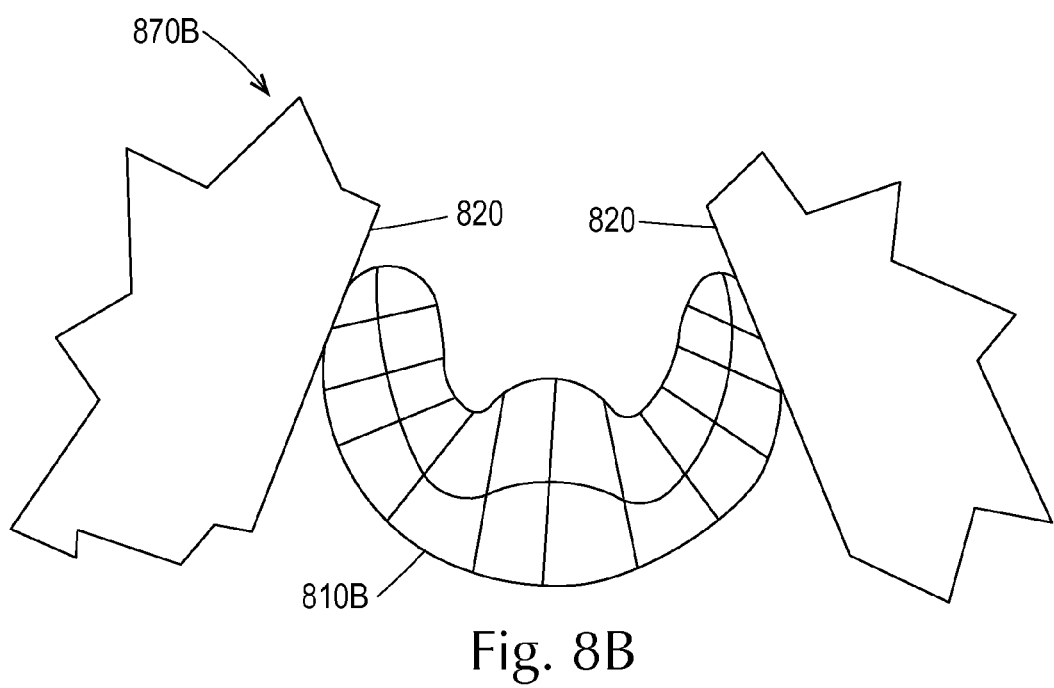
FIG. 8B is a view of FIG. 8A, wherein the article is in a swollen state.

FIG. 8B is a cross-sectional side view illustrating a computer based model 870B of the absorbent article 810B fitted to the portion of the human body 820, wherein the article 810B is in a swollen state.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A computer implemented method of simulation, comprising:
   representing at least a portion of a substrate with a computer based model, wherein the substrate is represented by a plurality of elements with each of the elements including an amount of the substrate;
   representing a domain space including the substrate;
   transforming the substrate to fit the domain space;
   representing a Non-Newtonian bodily exudate into the domain space with a computer based model of the bodily exudate;
   representing a Newtonian bodily exudate in to the domain space with a second computer based model of the bodily exudate;
   wherein the Non-Newtonian bodily exudate and the Newtonian bodily exudate are represented simultaneously;
   transforming the model of the substrate to form a computer based model on the distribution of the Newtonian and the Non-Newtonian bodily exudates using finite element analysis;
   wherein the transformation of the substrate is simultaneous to the distribution of the bodily exudates.

2. The method of claim 1, wherein the substrate is an absorbent article.

3. The method according to claim 1, wherein the step of dispensing the Newtonian exudate on the substrate further comprises determining an entrance point for the Newtonian exudate.

4. A method according to claim 2, wherein the absorbent article is selected from the group comprising a diaper, a sanitary napkin, or a tampon.

5. The method according to claim 1, wherein the step of representing a Non-Newtonian exudate further comprises determining the amount of the Non-Newtonian exudate.

6. The method according to claim 1, wherein the step of dispensing the Non-Newtonian exudate on the substrate further comprises determining an entrance point for the Non-Newtonian exudate.

7. A method according to claim 4, wherein the absorbent article is a diaper.

8. The method of claim 1, wherein the domain space represents a model of a human body and wherein the step of transforming the model of the substrate to form a computer based model on the distribution of the bodily exudate using finite element analysis further comprises determining which portions of the model of the human body came in contact with the bodily exudate and whether any bodily exudate remains in contact with that portion of the model of the human body.

9. The method of claim 1, wherein the step of transforming the model of the substrate to form a computer based model on the distribution of the bodily exudate using finite element analysis further comprises determining which portions of the substrate came in contact with the bodily exudate and whether any exudate remains in contact with that portion of the substrate.

\* \* \* \* \*